United States Patent
Owens et al.

(10) Patent No.: US 9,382,422 B2
(45) Date of Patent: Jul. 5, 2016

(54) ACELLULAR TISSUE MATRIX COMPOSITIONS FOR TISSUE REPAIR

(75) Inventors: Rick T. Owens, Stewartsville, NJ (US); Wendell Sun, Warrington, PA (US)

(73) Assignee: LifeCell Corporation, Branchburg, NJ (US)

( * ) Notice: Subject to any disclaimer, the term of this patent is extended or adjusted under 35 U.S.C. 154(b) by 707 days.

(21) Appl. No.: 12/747,441

(22) PCT Filed: Jul. 9, 2008

(86) PCT No.: PCT/US2008/069563
§ 371 (c)(1),
(2), (4) Date: Jun. 10, 2010

(87) PCT Pub. No.: WO2009/009620
PCT Pub. Date: Jan. 15, 2009

(65) Prior Publication Data
US 2010/0272782 A1    Oct. 28, 2010

Related U.S. Application Data

(60) Provisional application No. 60/948,793, filed on Jul. 10, 2007.

(51) Int. Cl.
*A61K 38/39* (2006.01)
*A61K 8/65* (2006.01)
*A61K 9/14* (2006.01)
*A61F 2/86* (2013.01)
*C08L 89/06* (2006.01)
*A61L 31/00* (2006.01)
*A61L 27/36* (2006.01)
*A61K 38/00* (2006.01)

(52) U.S. Cl.
CPC ............. *C08L 89/06* (2013.01); *A61L 27/36* (2013.01); *A61L 27/362* (2013.01); *A61L 27/3633* (2013.01); *A61L 31/005* (2013.01)

(58) Field of Classification Search
CPC .......................... A61L 29/045; A61L 2420/00
See application file for complete search history.

(56) References Cited

U.S. PATENT DOCUMENTS

| | | | |
|---|---|---|---|
| 5,284,655 A | 2/1994 | Bogdansky et al. | |
| 5,336,616 A | 8/1994 | Livesey et al. | |
| 5,364,756 A | 11/1994 | Livesey et al. | |
| 5,418,222 A * | 5/1995 | Song et al. | 424/443 |
| 5,993,844 A * | 11/1999 | Abraham et al. | 424/423 |
| 6,381,026 B1 | 4/2002 | Schiff et al. | |
| 6,933,326 B1 | 8/2005 | Griffey et al. | |
| 7,186,557 B2 * | 3/2007 | Marko | 435/377 |
| 7,326,571 B2 * | 2/2008 | Freyman | 435/372 |
| 7,358,284 B2 | 4/2008 | Griffey et al. | |
| 7,476,398 B1 * | 1/2009 | Doillon et al. | 424/423 |
| 7,498,412 B2 * | 3/2009 | Huang et al. | 530/356 |
| 7,767,114 B2 * | 8/2010 | Gordon et al. | 252/506 |
| 2003/0035843 A1 | 2/2003 | Livesey et al. | |
| 2003/0143207 A1 | 7/2003 | Livesey et al. | |
| 2003/0225355 A1 | 12/2003 | Butler | |
| 2004/0029478 A1 * | 2/2004 | Planck et al. | 442/318 |
| 2004/0253718 A1 * | 12/2004 | Marko | 435/368 |
| 2005/0012872 A1 * | 1/2005 | Baek | 349/38 |
| 2005/0013872 A1 | 1/2005 | Freyman | |
| 2005/0028228 A1 * | 2/2005 | McQuillan et al. | 800/17 |
| 2006/0073592 A1 | 4/2006 | Sun et al. | |
| 2006/0127375 A1 | 6/2006 | Livesey et al. | |
| 2006/0153815 A1 | 7/2006 | Seyda et al. | |
| 2006/0177513 A1 * | 8/2006 | Martin et al. | 424/489 |
| 2006/0210960 A1 | 9/2006 | Livesey et al. | |
| 2007/0014729 A1 | 1/2007 | Farhat et al. | |
| 2007/0202189 A1 * | 8/2007 | Ahlfors | 424/548 |
| 2007/0248575 A1 | 10/2007 | Connor et al. | |
| 2008/0281434 A1 * | 11/2008 | Schmidt et al. | 623/23.72 |
| 2010/0256774 A1 * | 10/2010 | Wang et al. | 623/23.63 |
| 2012/0053690 A1 * | 3/2012 | Frank | 623/8 |

FOREIGN PATENT DOCUMENTS

| | | |
|---|---|---|
| KR | 10-2005-0040186 A | 5/2005 |
| KR | 10-2005-0040187 A | 5/2005 |
| WO | WO 00/16822 A1 | 3/2000 |
| WO | WO 03/032735 A1 | 4/2003 |
| WO | WO 03084410 A1 * | 10/2003 |
| WO | WO 2009/009620 A2 | 1/2009 |

OTHER PUBLICATIONS

Butler et al. (2004) Reduction of Adhesions with Composite AlloDerm/Polypropylene Mesh Implants for Abdominal Wall Reconstruction, Plastic and Reconstructive Surgery, vol. 114, No. 2, pp. 464-473.*
Liang et al. (20110 Alpha1,3-galactosyltransferase knockout does not alter the properties of porcine extracellular matrix bioscaffolds, Acta Biomat., vol. 7, pp. 1719-1727.*
Chaplin, J.M. et al. "Use of an Acellular Dermal Allograft for Dural Replacement: An Experimental Study" *Neurosurgery* 45(2):320-327 (1999).
International Patent Application No. PCT/US2008/069563: International Search Report and Written Opinion; Date of Mailing: Jan. 9, 2009.
Tedder, M.E. et al., "Stabilized Collagen Scaffolds for Heart Valve Tissue Engineering" *Tissue Engineering: Part A* 00(00):1-12 (2008).
Kessler et al., "Chromatographic Fractionation of Acetic Acid-solubilied Rat Tail Tendon Collagen", *J. Bio. Chem.*, 235(4):989-994 (Apr. 1960).

* cited by examiner

*Primary Examiner* — Manjunath Rao
*Assistant Examiner* — Samuel Liu
(74) *Attorney, Agent, or Firm* — McCarter & English, LLP; Matthew R. Van Eman

(57) ABSTRACT

The invention provides tissue repair compositions and methods of making the tissue repair compositions. Also featured are methods of treatment using the tissue repair compositions and articles of manufacture that include the tissue repair compositions.

39 Claims, No Drawings

ACELLULAR TISSUE MATRIX COMPOSITIONS FOR TISSUE REPAIR

This is a national phase application under 35 U.S.C. §371 of International Application Number PCT/US2008/069563, filed on Jul. 9, 2008, and claims the benefit of priority under 35 U.S.C. §119 to U.S. Provisional Application No. 60/948,793, which was filed on Jul. 10, 2007 and is incorporated herein by reference.

TECHNICAL FIELD

This invention relates to tissue engineering, and more particularly to material that can be implanted in, or grafted to, vertebrate subjects for repair or amelioration of defective or damaged tissues.

BACKGROUND

Multicellular organisms, including mammals, are made up of tissues, that is, organized aggregates of specialized groups of cells of similar form and function. In many tissue types, the cells are also surrounded by an extracellular matrix (ECM), a complex mixture of carbohydrates and proteins that provides support and anchorage for cells. When tissues become damaged, an ordered series of physiological events must take place in a timely fashion for successful tissue regeneration to occur. The first events, termed the inflammatory phase, include blood clotting as well as the arrival at the wound site of cells that remove bacteria, debris and damaged tissue. Later, circulating stem cells migrate to the wound site and differentiate into tissue-specific cell types. Finally, the differentiated cells begin to produce and deposit new ECM.

Successful repair of defective or damaged tissue depends in part on providing conditions that allow for appropriate cellular regeneration and that minimize the likelihood of infection during the repair process.

SUMMARY

The inventors have found that fragments of an acellular tissue matrices (ATM), swollen in an acidic solution, can be dried to make a biocompatible tissue repair composition. In preferred embodiments, the suspension of ATM in acid solution is heated at mildly elevated temperatures prior to drying. Such biocompatible tissue repair compositions can provide a means of repairing multiple defective or damaged tissues while minimizing the promotion of adhesions or infection.

More specifically, a method of making a biocompatible mesh composition is provided. The method includes: a) incubating a plurality of fragments of an acellular tissue matrix (ATM) in an acidic solution to create a homogeneous suspension of swollen ATM fragments, wherein the acidic solution has a pH less than 3.0 and does not cause substantial irreversible denaturation of collagen fibers in the ATM; b) applying the homogeneous suspension to a biocompatible mesh substrate to create a coated mesh substrate; and c) drying the coated substrate to form a mesh composition. Steps (a) and (b) can be performed simultaneously.

The ATM can be or can include dermis from which all, or substantially all, viable cells have been removed. The ATM can include a tissue from which all, or substantially all, viable cells have been removed, wherein the tissue is selected from the group consisting of fascia, pericardial tissue, dura, umbilical cord tissue, placental tissue, cardiac valve tissue, ligament tissue, tendon tissue, arterial tissue, venous tissue, neural connective tissue, urinary bladder tissue, ureter tissue, and intestinal tissue. The ATM can be made from human tissue or non-human mammalian tissue. The non-human mammal can be a pig. In one aspect, the non-human mammal can be genetically engineered to lack expression of α-1,3-galactosyl residues. The non-human mammal can lack a functional α-1, 3-galactosyltransferase gene. The fragments of ATM can be particles of ATM.

In one aspect, the pH of the acidic solution can be below about 3.0. The pH can be from about 1.0 to about 3.0, from about 2.0 to about 3.0 or from about 1.5 to about 2.5. The pH can be about 1.4. In another aspect, the acidic solution can be a solution comprising an acid selected from the group consisting of acetic acid, ascorbic acid, boric acid, carbonic acid, citric acid, hydrochloric acid, lactic acid, tannic acid, phosphoric acid, and sulfuric acid. The acidic solution can include 0.1 M acetic acid. The acidic solution can include 0.04 M hydrochloric acid.

In one aspect, incubation step can be for a period from about 0.5 hours to about 12 hours. The incubation step can be for a period from about 1.0 to about 10.0 hours, from about 2.0 to about 6 hours or from about 2.5 to about 5 hours. The incubation step can be for a period of about 3 hours.

In one aspect, the incubating, the drying, or the incubating and the drying can be at a temperature of about 20° C. to about 42° C. The temperature can be from about 20° C. to about 30° C., from about 25° C. to about 35° C., from about 30° C. to about 40° C., from about 35° C. to about 38° C. or from about 37° C. to about 42° C. The temperature can be about 37° C. The temperature can be about 25° C.

In one aspect, the mesh substrate can be substantially non-absorbable. In another aspect, the mesh substrate can be absorbable. The absorbable mesh can be a polymer selected from the group consisting of polyhydroxyalkanoate, polyglycolic acid, poly-l-lactic acid, polylactic/polyglycolic acid (PLGA), polygalactin 910, and carboxymethyl cellulose. The polymer can include poly-4-hydroxybutyrate. The mesh substrate can be a synthetic substrate; the synthetic substrate can include polypropylene.

In another aspect, the drying can include drying in a nitrogen atmosphere or freeze-drying.

In another aspect, the method of making a biocompatible mesh composition can include: a) incubating a plurality of fragments of a porcine acellular dermal matrix for about 3 hours at a temperature of about 37° C. in an 0.1 M acetic acid solution to create a homogeneous suspension of swollen fragments, wherein the acidic solution has a pH of about 2.6 and does not cause substantial irreversible denaturation of collagen fibers in the porcine acellular dermal matrix; b) applying the homogeneous suspension to a biocompatible polypropylene mesh substrate to create a coated mesh substrate; and c) drying the coated substrate in a nitrogen atmosphere to form a mesh composition.

In another embodiment, the invention provides a biocompatible mesh composition made by a) incubating a plurality of fragments of an ATM in an acidic solution to create a homogeneous suspension of swollen ATM fragments, wherein the acidic solution has a pH less than 3.0 and does not cause substantial irreversible denaturation of collagen fibers in the ATM; b) applying the homogeneous suspension to a biocompatible mesh substrate to create a coated mesh substrate; and c) drying the coated substrate to form a mesh composition. Steps (a) and (b) can be performed simultaneously.

The ATM can be or can include dermis from which all, or substantially all, viable cells have been removed. The ATM can include a tissue from which all, or substantially all, viable cells have been removed, wherein the tissue is selected from the group consisting of fascia, pericardial tissue, dura, umbilical cord tissue, placental tissue, cardiac valve tissue, ligament tissue, tendon tissue, arterial tissue, venous tissue, neural connective tissue, urinary bladder tissue, ureter tissue, and intestinal tissue. The ATM can be made from human tissue or non-human mammalian tissue. The non-human mammal can be a pig. In some embodiments, the non-human mammal can be genetically engineered to lack expression of α-1,3-galactosyl residues. The non-human mammal can lack a functional α-1,3-galactosyltransferase gene. The fragments of ATM can be particles of ATM.

In one aspect, the pH of the acidic solution can be below about 3.0. The pH can be from about 1.0 to about 3.0, from about 2.0 to about 3.0 or from about 1.5 to about 2.5. The pH can be about 1.4. In another aspect, the acidic solution can be a solution comprising an acid selected from the group consisting of acetic acid, ascorbic acid, boric acid, carbonic acid, citric acid, hydrochloric acid, lactic acid, tannic acid, phosphoric acid, and sulfuric acid. The acidic solution can include 0.1 M acetic acid. The acidic solution can include 0.04 M hydrochloric acid.

In one aspect, incubation step can be for a period from about 0.5 hours to about 12 hours. The incubation step can be for a period from about 1.0 to about 10.0 hours. The incubation step can be for a period from about 2.0 to about 6 hours or from about 2.5 to about 5 hours. The incubation step can for a period of about 3 hours.

In one aspect, the incubating, the drying, or the incubating and the drying can be at a temperature of about 20° C. to about 42° C. The temperature can be from about 20° C. to about 30° C., from about 25° C. to about 35° C., from about 30° C. to about 40° C., from about 35° C. to about 38° C., or from about 37° C. to about 42° C. The temperature can be about 37° C. The temperature can be about 25° C.

In one aspect, the mesh substrate can be substantially non-absorbable. In another aspect, the mesh substrate can be absorbable. The absorbable mesh can be a polymer selected from the group consisting of polyhydroxyalkanoate, polyglycolic acid, poly-l-lactic acid, polylactic/polyglycolic acid (PLGA), polygalactin 910, and carboxymethyl cellulose. The polymer can include poly-4-hydroxybutyrate. The mesh substrate can be a synthetic substrate; the synthetic substrate can include polypropylene.

In another aspect, the drying can include drying in a nitrogen atmosphere or freeze-drying.

In another embodiment, a biocompatible mesh composition is provided. The composition includes a coated mesh substrate, wherein the coating on the mesh substrate includes a dried ATM suspension. In one aspect, the composition includes an ATM suspension including a plurality of acellular tissue matrix (ATM) fragments swollen in an acidic solution, wherein the acidic solution has a pH less than 3.0 and does not cause substantial irreversible denaturation of collagen fibers in the ATM, and wherein the ATM fragments are incubated at a temperature of about 30° C. to about 42° C.

The ATM can be or can include dermis from which all, or substantially all, viable cells have been removed. The ATM can include a tissue from which all, or substantially all, viable cells have been removed, wherein the tissue is selected from the group consisting of fascia, pericardial tissue, dura, umbilical cord tissue, placental tissue, cardiac valve tissue, ligament tissue, tendon tissue, arterial tissue, venous tissue, neural connective tissue, urinary bladder tissue, ureter tissue, and intestinal tissue. The ATM can be made from human tissue or non-human mammalian tissue. The non-human mammal can be a pig. In some embodiments, the non-human mammal can be genetically engineered to lack expression of α-1,3-galactosyl residues. The non-human mammal can lack a functional α-1,3-galactosyltransferase gene. The fragments of ATM can be particles of ATM.

In one aspect, the pH can be below about 3.0. The pH can be from about 1.0 to about 3.0, from about 2.0 to about 3.0 or from about 1.5 to about 2.5. The pH can be about 1.4. In another aspect, the acidic solution can be a solution comprising an acid selected from the group consisting of acetic acid, ascorbic acid, boric acid, carbonic acid, citric acid, hydrochloric acid, lactic acid, tannic acid, phosphoric acid, and sulfuric acid. The acidic solution can include 0.1 M acetic acid. The acidic solution can include 0.04 M hydrochloric acid.

In one aspect, incubation step can be for a period from about 0.5 hours to about 12 hours. The incubation step can be for a period from about 1.0 to about 10.0 hours. The incubation step can be for a period from about 2.0 to about 6 hours or from about 2.5 to about 5 hours. The incubation step can for a period of about 3 hours.

In one aspect, the incubating, the drying, or the incubating and the drying can be at a temperature of about 20° C. to about 42° C. The temperature can be from about 20° C. to about 30° C., from about 25° C. to about 35° C., from about 30° C. to about 40° C., from about 35° C. to about 38° C., or from about 37° C. to about 42° C. The temperature can be about 37° C. The temperature can be about 25° C.

In one aspect, the mesh substrate can be substantially non-absorbable. In another aspect, the mesh substrate can be absorbable. The absorbable mesh can be a polymer selected from the group consisting of polyhydroxyalkanoate, polyglycolic acid, poly-l-lactic acid, polylactic/polyglycolic acid (PLGA), polygalactin 910, and carboxymethyl cellulose. The polymer can include poly-4-hydroxybutyrate. The mesh substrate can be a synthetic substrate; the synthetic substrate can include polypropylene.

In another aspect, the drying can include drying in a nitrogen atmosphere or freeze-drying.

In another embodiment, a method of ameliorating or repairing an organ or tissue is provided. The method includes a) identifying a mammalian subject as having an organ or tissue in need of amelioration or repair; and b) placing any of the above-described biocompatible mesh compositions in or on the organ or tissue. The mammalian subject can be human. The recipient organ or tissue can be selected from the group consisting of abdominal wall tissue, abdominal muscle, and smooth muscle tissue. The subject can have a defect in need of repair selected from the group consisting of an inguinal hernia, a femoral hernia, a ventral hernia, an abdominal hernia, an incisional hernia, a hiatal hernia, a diaphragmatic hernia, an umbilical hernia, fascial weakness in the chest, fascial weakness in the abdominal wall, and pelvic organ prolapse.

In another embodiment, articles of manufacture are provided. An article of manufacture can include a biocompatible mesh composition including a coated mesh substrate, wherein the coating on the mesh substrate includes a dried ATM suspension; and b) packaging material, or a package insert, comprising instructions for a method of ameliorating or repairing an organ or tissue. The method can include i) identifying a mammalian subject as having a recipient organ or tissue in need of amelioration or repair; and ii) placing the biocompatible mesh composition in or on the organ or tissue.

In another embodiment, a method of making a biocompatible dermal film composition is provided. The method can include swelling a plurality of fragments of an acellular tissue matrix (ATM) in an acidic solution to create a homogeneous suspension, wherein the acidic solution has a pH less than 3.0 and does not cause substantial irreversible denaturation of collagen fibers in the ATM; b) incubating the homogeneous suspension of ATM at a temperature of about 20° C. to about 42° C.; and c) drying the homogeneous suspension to form a dermal film composition.

In the above described methods, compositions and articles of manufacture, the recited embodiments can be combined in any combination desired.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

The materials and methods provided herein can be used to make a biocompatible tissue repair composition that can be implanted into an a damaged or defective organ or tissue to facilitate the repair of the damaged or defective organ or tissue. As used herein, a "biocompatible" composition is one that has the ability to support cellular activity necessary for complete or partial tissue regeneration, but does not stimulate a significant local or systemic inflammatory or immunological response in the host. As used herein, a "significant local or systemic inflammatory or immunological response in the host" is a local or systemic inflammatory or immunological response that partially or completely prevents tissue regeneration by a composition of the invention.

I. Composition Components

The composition of the invention is made by swelling ATM fragments in an acidic solution and then drying the resulting swollen ATM fragment suspension, preferably onto one surface, or both surfaces, of a mesh substrate. The coating of implantable medical devices with the compositions provided herein in order to attenuate a foreign body response is also contemplated. Examples of suitable devices include, without limitation, artificial joints, vascular grafts, artificial valves, cardiac pacemakers, cardiac defibrillators, muscle stimulators, neurological stimulators, cochlear implants, monitoring devices, drug pumps and left ventricular assist devices.

Acellular Tissue Matrices

As used herein, an "acellular tissue matrix" ("ATM") is a tissue-derived structure that is made from any of a wide range of collagen-containing tissues by removing all, or substantially all, viable cells and, preferably, all detectable dead cells, subcellular components and/or debris generated by dead or dying cells. As used herein, an "acellular matrix" is a matrix that: (a) is made from any of a wide range of collagen-based tissues; (b) is acellular; and (c) retains the biological and structural functions possessed by the native tissue or organ from which it was made. Biological functions retained by matrices include cell recognition and cell binding as well as the ability to support cell spreading, cell proliferation, and cell differentiation. Such functions are provided by undenatured collagenous proteins (e.g., type I collagen) and a variety of non-collagenous molecules (e.g., proteins that serve as ligands for either molecules such as integrin receptors, molecules with high charge density such glycosaminoglycans (e.g., hyaluronan) or proteoglycans, or other adhesins). Structural functions retained by useful acellular matrices include maintenance of histological architecture, maintenance of the three-dimensional array of the tissue's components and physical characteristics such as strength, elasticity, and durability, defined porosity, and retention of macromolecules. The efficiency of the biological functions of an acellular matrix can be measured, for example, by its ability to support cell proliferation and is at least 50% (e.g., at least: 50%; 60%; 70%; 80%; 90%; 95%; 98%; 99%; 99.5%; 100%; or more than 100%) of those of the native tissue or organ from which the acellular matrix is made. In addition, the integrity of the basement membrane in the acellular matrices, as measured by electron microscopy and/or immunohistochemistry, is at least 70% of that of the native tissue or organ from which the acellular matrix is made. As used herein, an ATM lacking "substantially all viable cells" is an ATM in which the concentration of viable cells is less than 1% (e.g., less than: 0.1%; 0.01%; 0.001%; 0.0001%; 0.00001%; 0.000001%; or 0.0%) of that in the tissue or organ from which the ATM was made. The ATM useful for the invention are preferably also substantially lack dead cells and/or cell debris that may be present after killing the cells in the ATM. An ATM "substantially lacking dead cells and/or cell debris" is one that contains less than 10% (i.e., less than: 8%; 5%; 1%; 0.1%; 0.001%; 0.0001%; or less) of the dead cells and/or cell debris present in the ATM following a cell removal process.

ATM made from dermis are referred to herein in some instances as "acellular dermal matrices" ("ADM").

The ATM of the invention can have or lack an epithelial basement membrane. The epithelial basement membrane is a thin sheet of extracellular material contiguous with the basilar aspect of epithelial cells. Sheets of aggregated epithelial cells form an epithelium. Thus, for example, the epithelium of skin is called the epidermis, and the skin epithelial basement membrane lies between the epidermis and the dermis. The epithelial basement membrane is a specialized extracellular matrix that provides a barrier function and an attachment surface for epithelial-like cells; however, it does not contribute any significant structural or biomechanical role to the underlying tissue (e.g., dermis). Unique components of epithelial basement membranes include, for example, laminin, collagen type VII, and nidogen. The unique temporal and spatial organization of the epithelial basement membrane distinguish it from, e.g., the dermal extracellular matrix. In some embodiments, the presence of the epithelial basement membrane in an ATM could be disadvantageous in that the epithelial basement membrane can contain a variety of species-specific components that could elicit the production of antibodies, and/or bind to preformed antibodies, in xenogeneic graft recipients of the acellular matrix. In addition, the epithelial basement membrane can act as barrier to diffusion of cells and/or soluble factors (e.g., chemoattractants) and to cell infiltration. Its presence in an ATM can thus significantly delay formation of new tissue from the ATM in a recipient animal. As used herein, an ATM that "substantially lacks" an epithelial basement membrane is an acellular tissue matrix containing less than 5% (e.g., less than: 3%; 2%; 1%; 0.5%; 0.25%; 0.1%; 0.01%; 0.001%; or even less than 0.001%) of the epithelial basement membrane possessed by the corresponding unprocessed tissue from which the ATM was derived.

The ATM retain the biological and structural attributes of the tissues from which they are made, including cell recognition and cell binding as well as the ability to support cell spreading, cell proliferation, and cell differentiation. Such functions are provided by undenatured collagenous proteins (e.g., type I collagen) and a variety of non-collagenous molecules (e.g., proteins that serve as ligands for either molecules such as integrin receptors, molecules with high charge density such glycosaminoglycans (e.g., hyaluronan) or proteoglycans, or other adhesins). Structural functions retained by useful ATM include maintenance of histological architecture, maintenance of the three-dimensional array of the tissue's components and physical characteristics such as strength, elasticity, and durability, defined porosity, and retention of macromolecules. The efficiency of the biological functions of an ATM can be measured, for example, by the ability of the ATM to support cell (e.g., epithelial cell) proliferation and is at least 30% (e.g., at least: 40%; 50%; 60%; 70%; 80%; 90%; 95%; 98%; 99%; 99.5%; 100%; or more than 100%) of that of the native tissue or organ from which the ATM is made. It is not necessary that the ATM be made from tissue that is identical to the surrounding host tissue but should simply be amenable to being remodeled by invading or infiltrating cells such as differentiated cells of the relevant host tissue, stem cells such as mesenchymal stem cells, or progenitor cells. It is understood that the ATM can be produced from any collagen-containing soft tissue and muscular skeleton (e.g., dermis, fascia, pericardium, dura, umbilical cords, placentae, cardiac valves, ligaments, tendons, vascular tissue (arteries and veins such as saphenous veins), neural connective tissue, urinary bladder tissue, ureter tissue, or intestinal tissue), as long as the above-described properties are retained by the matrix.

An ATM useful for the invention can optionally be made from a recipient's own collagen-based tissue. Furthermore, while an ATM will generally have been made from one or more individuals of the same species as the recipient of the tissue repair composition, this is not necessarily the case. Thus, for example, an ATM can have been made from a porcine tissue and be used to make a tissue repair composition that can be implanted in a human patient. Species that can serve as recipients of a tissue repair composition and donors of tissues or organs for the production of the ATM component of the tissue repair composition can include, without limitation, mammals, such as humans, non-human primates (e.g., monkeys, baboons, or chimpanzees), pigs, cows, horses, goats, sheep, dogs, cats, rabbits, guinea pigs, gerbils, hamsters, rats, or mice. Moreover, different breeds of animals within a species (e.g., Yucatan mini-pigs or Yorkshire pigs) can be used.

Of particular interest as donors are animals (e.g., pigs and cows) that have been genetically engineered to lack the terminal galactose-α-1,3-galactose moiety. For descriptions of appropriate animals, see co-pending U.S. Published Application No. 2005/0028228 A1 and U.S. Pat. No. 6,166,288, the disclosures of which are incorporated herein by reference in their entirety. A major problem of xenotransplantation in recipient animals (e.g., humans) that do not express the enzyme UDP-galactose: β-D-galactosyl-1,4-N-acetyl-D-glucosaminide α-1,3 galactosyl-transferase (α-1,3 galactosyltransferase; "α-GT") that catalyzes the formation of the terminal disaccharide structure, galactose α-1,3 galactose ("α-gal"), is the hyperacute rejection of xenografts in such recipients. This rejection is largely, if not exclusively, due to the action of antibodies specific for the α-gal epitope on the surface of cells in the xenograft. Transgenic animals (e.g., pigs and cows) have been derived which lack, or substantially lack, functional α-GT and thus also lack, or substantially lack, α-gal epitopes.

Methods of making transgenic animals, and in particular gene-disrupted transgenic animals, are well known in the art. Methods of making gene-disrupted animals involve, for example, incorporating a disrupted form of a gene of interest into the germline of an individual of a species. The gene can be disrupted so that no protein product (e.g., α-GT) is produced or a protein product is produced that lacks the activity, or substantially lacks the activity, of the native protein. As used herein, a α-GT protein "substantially lacking α-GT activity" is an α-GT protein that has less than 5% (e.g., less than: 4%; 2%; 1%; 0.1%; 0.01%; 0.001%; or even less than 0.001%) of the ability of wild-type α-GT to generate α-gal epitopes. Methods of disrupting genes, and in particular, the α-GT gene, are known in the art and generally involve the process known as homologous recombination. In this process, one or both copies of a wild-type gene of interest can be disrupted by inserting a sequence into the wild-type gene(s) such that no transcript is produced from the gene(s); or a transcript is produced from which no protein is translated; or a transcript is produced that directs the synthesis of a protein that lacks, or substantially lacks, the functional activity of the protein of interest. Such constructs typically include all or part of the genomic sequence of the gene of interest and contain, within that genomic sequence, a sequence that will disrupt expression of the gene of interest in one of the ways described above. The sequence used to disrupt expression of the gene can be a sequence encoding a protein that confers antibiotic resistance (e.g., neomycin resistance) on target cells that have incorporated the construct into their genomes. Such a coding sequence facilitates the in vitro selection of cells that have incorporated the genetic construct into their genomes. Additional drug selection methodologies known in the art can be used to select cells in which recombination between the construct and at least one copy of the targeted gene has occurred.

In some methods of generating gene disrupted animals, totipotent cells (i.e., cells capable of giving rise to all cell types of an embryo) can be used as target cells. Such cells include, for example embryonic stem (ES) cells (in the form of ES cell lines) or fertilized eggs (oocytes). A population of ES cells in which at least one copy of the gene of interest is disrupted can be injected into appropriate blastocysts and the injected blastocysts can be implanted into foster mothers. Alternatively, fertilized eggs injected with the gene-disrupting construct of interest can be implanted in the foster mothers. Moreover, oocytes implanted in foster mothers can be those that have been enucleated and injected with nuclei from successfully gene-disrupted ES cells [Campbell et al., (1996) Nature 380: 64-66]. Resulting mutation-containing offspring arising in such mother foster mothers can be identified and, from these founder animals, distinct animal lines can be produced using breeding and selection methods known to those in the art.

Standard and gene-disrupted transgenic animals can also be produced using somatic cells (e.g., fetal fibroblasts) as target cells for the gene-disruption. Such cells grow much faster and are more easily handled in vitro than, for example, ES cells, thus facilitating the gene disruption and subsequent gene-disrupted cell selection procedures. Once a line of gene-disrupted somatic cells has been selected in vitro, nuclei from the gene-disrupted somatic cells can be incorporated into totipotent cells (e.g., ES cells or oocytes), which are then handled as described above. Methods for nuclear transplantation are known to those in the art and can include techniques such as, for example, cell fusion or nuclear transplantation.

Most commonly, the gene disruption procedures result in disruption of only one allele of a gene of interest. In these cases, the transgenic animals will be heterozygous for the disrupted gene. Breeding of such heterozygotes and appropriate selection procedures familiar to those in the art can then be used to derive animals that are homozygous for the disrupted gene. Naturally, such breeding procedures are not necessary where the gene disruption procedure described above resulted in disruption of both alleles of the gene of interest.

As an alternative to the use of genetically engineered animals, specific enzymatic treatments may be used for removal of the terminal galactose-α-1,3-galactose. Enzymatic treatment of ATM with an α-1,3-galactosidase can be performed using a specific glycosidase that has α-1,3-galactosidase activity, for example, coffee bean α-1,3-glactosidase. This enzyme can be derived from either natural sources or produced using the *Pichia pastoris* expression system or any other recombinant system capable of producing a functional α-1,3-glalactosidase.

For the production of tissue repair composition, ATM in the form of fragments (i.e., particles, threads or fibers) are generally used (see below). The ATM can be produced by any of a variety of methods. All that is required is that the steps used in their production result in matrices with the above-described biological and structural properties. Particularly useful methods of production include those described in U.S. Pat. Nos. 4,865,871; 5,366,616; 6,933,326 and copending U.S. Published Application Nos. 2003/0035843 A1, and 2005/0028228 A1, all of which are incorporated herein by reference in their entirety.

In brief, the steps involved in the production of an ATM generally include harvesting the tissue from a donor (e.g., a human cadaver or any of the above-listed mammals), chemical treatment so as to stabilize the tissue and avoid biochemical and structural degradation together with, or followed by, cell removal under conditions which similarly preserve biological and structural function. The ATM can optionally be treated with a cryopreservation agent and cryopreserved and, optionally, freeze-dried, again under conditions necessary to maintain the described biological and structural properties of the matrix. After freezing or freeze drying, the tissue can be fragmented, e.g., pulverized or micronized to produce a particulate ATM under similar function-preserving conditions. All steps are generally carried out under aseptic, preferably sterile, conditions.

An exemplary method of producing ATM, which is described in greater detail in U.S. Pat. No. 5,366,616, is summarized below.

After removal from the donor, the tissue is placed in an initial stabilizing solution. The initial stabilizing solution arrests and prevents osmotic, hypoxic, autolytic, and proteolytic degradation, protects against microbial contamination, and reduces mechanical damage that can occur with tissues that contain, for example, smooth muscle components (e.g., blood vessels). The stabilizing solution generally contains an appropriate buffer, one or more antioxidants, one or more oncotic agents, one or more antibiotics, one or more protease inhibitors, and in some cases, a smooth muscle relaxant.

The tissue is then placed in a processing solution to remove viable cells (e.g., epithelial cells, endothelial cells, smooth muscle cells, and fibroblasts) from the structural matrix without damaging the basement membrane complex or the biological and structural integrity of the collagen matrix. The processing solution generally contains an appropriate buffer, salt, an antibiotic, one or more detergents, one or more agents to prevent cross-linking, one or more protease inhibitors, and/or one or more enzymes.

An appropriate buffer can be an organic buffer, for example, 2-(N-morpholino)ethanesulfonic acid (MES), 3-(N-morpholine)propanesulfonic acid (MPOS) and N-2-hydroxyethylpiperazine-N'-2-ethane-sulfonic acid (HEPES). Alternatively, a low salt or physiological buffer, including phosphate, bicarbonate and acetate-citrate, may be more appropriate in certain applications. Salts can include common physiologic salts such as sodium chloride or potassium chloride. Antibiotics can include, for example, penicillin, streptomycin, gentamicin kanamycin, neomycin, bacitracin, and vancomycin. Additionally, anti-fungal agents may be employed, including amphotericin-B, nystatin, and polymyxin. Suitable detergents include without limitation, for example, sodium deoxycholate, Triton-X-100™ (Rohm and Haas, Philadelphia, Pa.), polyoxyethylene (20) sorbitan mono-oleate (Tween 20); polyoxyethylene (80) sorbitan mono-oleate (Tween 80); 3-[(3-chloramidopropyl)-dimethylamino]-1-propane sulfonate; octyl glucoside; and sodium dodecyl sulfate. Agents that inhibit or prevent the formation of cross-links can include ethylenediaminetetraacetic acid (EDTA), ascorbic acid and other free radical scavengers. Examples of useful protease inhibitors include, without limitation, N-ethylmaleimide (NEM), phenylmethylsulfonyl fluoride (PMSF), ethylenediaminetetraacetic acid (EDTA), ethylene glycol-bis (2-aminoethyl ether)-N,N,N',N'-tetraacetic acid (EGTA), leupeptin, ammonium chloride, elevated pH and apoprotinin. Examples of useful enzymes include, without limitation, dispase II, trypsin, and thermolysin. In some embodiments, an osmotic balancing agent can be included in the processing solution to provide a colloid osmotic balance between the solution and the tissue, thus preventing the diffusion of endogenous proteoglycans from the tissue to the solution. The osmotic balancing agent can be, for example, without limitation, a proteoglycan, e.g., chondroitin sulfate, heparin sulfate, or dermatan sulfate, or a polymer, e.g., dextran or polyvinyl pyrolodone (PVP), or an amino acid, e.g., glycine or valine.

Treatment of the tissue must be with a processing solution containing active agents at a concentration and for a time period such that, after processing, the tissue retains the biological and structural attributes of the native unprocessed tissue (see the above description of ATM).

After decellularization, the tissue can be frozen (i.e., cryopreserved) and optionally, freeze-dried. Before freezing, the tissue can be incubated in a cryopreservation solution. This solution generally contains one or more cryoprotectants to minimize ice crystal damage to the structural matrix that could occur during freezing. Examples of useful cryoprotectants are provided in U.S. Pat. No. 5,336,616. If the tissue is to be freeze-dried, the solution will generally also contain one or more dry-protective components, to minimize structural damage during drying and may include a combination of an organic solvent and water which undergoes neither expansion or contraction during freezing. The cryoprotective and dry-protective agents can be the same one or more substances. If the tissue is not going to be freeze-dried, it can be frozen by placing it (in a sterilized container) in a freezer at about −80° C., or by plunging it into sterile liquid nitrogen, and then storing at a temperature below −160° C. until use. The sample can be thawed prior to use by, for example, immersing a sterile non-permeable vessel (see below) containing the sample into a water bath at about 37° C. or by allowing the tissue to come to room temperature under ambient conditions.

If the tissue is to be frozen and freeze-dried, following incubation in the cryopreservation solution, the tissue can be packaged inside a sterile vessel that is permeable to water vapor yet impermeable to bacteria, e.g., a water vapor permeable pouch or glass vial. One side of a preferred pouch consists of medical grade porous Tyvek® membrane, a trademarked product of DuPont Company of Wilmington, Del. This membrane is porous to water vapor and impervious to bacteria and dust. The Tyvek® membrane is heat sealed to a impermeable polyethylene laminate sheet, leaving one side open, thus forming a two-sided pouch. The open pouch is sterilized by irradiation (e.g., γ-irradiation) prior to use. The tissue is aseptically placed (through the open side) into the sterile pouch. The open side is then aseptically heat sealed to close the pouch. The packaged tissue is henceforth protected from microbial contamination throughout subsequent processing steps.

The vessel containing the tissue is cooled to a low temperature at a specified rate which is compatible with the specific cryoprotectant formulation to minimize the freezing damage. See U.S. Pat. No. 5,336,616 for examples of appropriate cooling protocols. The tissue is then dried at a low temperature under vacuum conditions, such that water vapor is removed sequentially from each ice crystal phase.

At the completion of the drying of the samples in the water vapor permeable vessel, the vacuum of the freeze drying apparatus is reversed with a dry inert gas such as nitrogen, helium or argon. While being maintained in the same gaseous environment, the semipermeable vessel is placed inside an impervious (i.e., impermeable to water vapor as well as microorganisms) vessel (e.g., a pouch) which is further sealed, e.g., by heat and/or pressure. Where the tissue sample was frozen and dried in a glass vial, the vial is sealed under vacuum with an appropriate inert stopper and the vacuum of the drying apparatus reversed with an inert gas prior to unloading. In either case, the final product is hermetically sealed in an inert gaseous atmosphere. The freeze-dried tissue may be stored under refrigerated conditions until fragmentation or, if desired, rehydration.

ATM fragments are either particles (particulate), fibers, or threads.

Particulate ATM have a generally spherical or even irregular shape, with the longest dimension being not greater than 1000 microns. Particulate ATM can be made from any of the above described non-particulate ATM by any process that results in the preservation of the biological and structural functions described above and, in particular, damage to collagen fibers, including sheared fiber ends, should be minimized.

One appropriate method for making particulate ATM is described in U.S. Pat. No. 6,933,326, the disclosure which is herein incorporated herein by reference in its entirety. The process is briefly described below with respect to a freeze-dried dermal ATM (acellular dermal matrix; ADM) but one of skill in the art could readily adapt the method for use with frozen or freeze-dried ATM derived from any of the other tissues listed herein.

The ADM can be cut into strips (using, for example, a Zimmer mesher fitted with a non-interrupting "continuous" cutting wheel). The resulting long strips are then cut into lengths of about 1 cm to about 2 cm. A homogenizer and sterilized homogenizer probe (e.g., a LabTeck Macro homogenizer available from OMNI International, Warrenton, Va.) is assembled and cooled to cryogenic temperatures (i.e., about −196° C. to about −160° C.) using sterile liquid nitrogen which is poured into the homogenizer tower. Once the homogenizer has reached a cryogenic temperature, cut pieces of ADM are added to the homogenizing tower containing the liquid nitrogen. The homogenizer is then activated so as to cryogenically fracture the pieces of ADM. The time and duration of the cryogenic fracturing step depends upon the homogenizer utilized, the size of the homogenizing chamber, and the speed and time at which the homogenizer is operated, and are readily determinable by one skilled in the art. As an alternative, the cryofracturing process can be conducted in cryomill cooled to a cryogenic temperature.

The cryofractured particulate ATM is, optionally, sorted by particle size by washing the product of the homogenization with sterile liquid nitrogen through a series of metal screens that have also been cooled to a cryogenic temperature. It is generally useful to eliminate large undesired particles with a screen with a relatively large pore size before proceeding to one (or more screens) with a smaller pore size. Once isolated, the particles can be freeze-dried to ensure that any residual moisture that may have been absorbed during the procedure is removed. The final product is a powder (usually white or off-white) generally having a particle size of about 1 micron to about 900 microns, about 30 microns to about 750 microns, or about 150 to about 300 microns.

ATM fragments can also be fibers or threads. Such fibers or threads would generally not be greater than 5 cm (e.g., not greater than: 4.5 cm; 4.0 cm; 3.5 cm; 3.0 cm; 2.5 cm; 2.0 cm; 1.5 cm; 1.0 cm; 0.5 cm; 0.25 cm; 0.1 cm; 0.05 cm; or 0.02 cm) in length and not greater than 3 mm (e.g., not greater than: 2.5 mm; 2.0 mm; 1.5 mm; 1.0 mm; 0.5 mm; 0.2 mm; 0.1 mm; 0.05 mm; 0.02 mm; or 0.01 mm) at their widest point. Methods of producing fibers and threads from frozen or freeze-dried ATM would be apparent to those skilled in the art and include both manual or machine cutting of the frozen or freeze-dried ATM.

One highly suitable freeze-dried ATM is produced from human dermis by the LifeCell Corporation (Branchburg, N.J.) and marketed in the form of small sheets as AlloDerm®. Such sheets are marketed by the LifeCell Corporation as rectangular sheets with the dimensions of, for example, 1 cm×2 cm, 3 cm×7 cm, 4 cm×8 cm, 5 cm×10 cm, 4 cm×12 cm, and 6 cm×12 cm. The cryoprotectant used for freezing and drying AlloDerm® is a solution of 35% maltodextrin and 10 mM ethylenediaminetetraacetate (EDTA). Thus, the final dried product contains about 60% by weight ATM and about 40% by weight maltodextrin. The LifeCell Corporation also makes an analogous product from porcine dermis (designated XenoDerm™) having the same proportions of ATM and maltodextrin as AlioDerm®. In addition, the LifeCell Corporation markets a particulate acellular dermal matrix made by cryofracturing AlloDerm® (as described above) under the name Cymetra®. The particle size for Cymetra® is in the range of about 60 microns to about 150 microns as determined by mass. The particles of particulate or pulverized (powdered) ATM will be less than 1.0 mm in their longest dimension. Pieces of ATM with dimensions greater than this are non-particulate acellular matrices.

Mesh Substrates

In some embodiments, the biocompatible tissue repair composition can include a mesh substrate. Any biocompatible mesh substrate, e.g., a surgical mesh, can be used.

Surgical mesh substrates are multifilament woven materials that are available in many forms and have been produced from a variety of synthetic and natural materials. Meshes can be broadly classified according to filament structure, pore size and weight. Filament structure can be monofilament, multifilament or multifilament fibers formed from monofilament materials. Mesh pore sizes can range from between about 200μ to about 5000μ. Small pore sizes, e.g., 1000μ or less, are typical of heavyweight meshes, while larger pore sizes, e.g., greater than 1000μ are characteristic of lightweight meshes. Mesh weight is expressed as g/m², with heavyweight meshes having densities of about 80-100 g/m² and lightweight meshes having densities in the range of 25-45 g/m².

The mesh substrate can be made of a non-absorbable material, an absorbable material or a material that is a combination of both non-absorbable and absorbable materials. "Absorbable material" is defined herein as any material that can be degraded in the body of a mammalian recipient by endogenous enzymatic or cellular processes. Depending upon the particular composition of the material, the degradation products can be recycled via normal metabolic pathways or excreted through one or more organ systems. Naturally, a "non-absorbable material" is one that cannot be degraded in the body of a mammalian recipient by endogenous enzymatic or cellular processes.

Polymers used to make non-absorbable meshes include polypropylene, polyester, i.e., polyethylene terephthalate, or polytetrafluoroethylene (PTFE). Examples of commercially available polypropylene meshes include: Marlex™ (CR Bard, Inc., Cranston R.I.), Visilex® (CR Bard, Inc., Cranston R.I.), PerFix® Plug (CR Bard, Inc., Cranston R.I.), Kugel™ Hernia Patch (CR Bard, Inc., Cranston R.I.), 3DMax® (CR Bard, Inc., Cranston R.I.), Prolene™ (Ethicon, Inc., Somerville, N.J.), Surgipro™ (Autosuture, U.S. Surgical, Norwalk, Conn.), Prolite™ (Atrium Medical Co., Hudson, N.H.), Prolite Ultra™ (Atrium Medical Co., Hudson, N.H.), Trelex™ (Meadox Medical, Oakland, N.J.), and Parietene® (Sofradim, Trévoux, France). Examples of commercially available polyester meshes include Mersilene™ (Ethicon, Inc., Somerville, N.J.) and Parietex® (Sofradim, Trevoux, France). Examples of commercially available PTFE meshes include Goretex® (W. L. Gore & Associates, Newark, Del.), Dualmesh® (W. L. Gore & Associates, Newark, Del.), Dualmesh® Plus (W. L. Gore & Associates, Newark, Del.), Dulex® (CR Bard, Inc., Cranston R.I.), and Reconix® (CR Bard, Inc., Cranston R.I.).

Absorbable meshes are also available from commercial sources. Polymers used to make absorbable meshes can include polyglycolic acid (Dexon™, Syneture™, U.S. Surgical, Norwalk, Conn.), poly-l-lactic acid, polyglactin 910 (Vicryl™, Ethicon, Somerville, N.J.), or polyhydroxylalkaoate derivatives such as poly-4-hydroxybutyrate (Tepha, Cambridge, Mass.).

Composite meshes, i.e., meshes that include both absorbable and non-absorbable materials can be made either from combinations of the materials described above or from additional materials. Examples of commercially available composite meshes include polypropylene/PTFE: Composix® (CR Bard, Inc., Cranston R.I.), Composix® E/X (CR Bard, Inc., Cranston R.I.), and Ventralex® (CR Bard, Inc., Cranston R.I.); polypropylene/cellulose: Proceed™ (Ethicon, Inc., Somerville, N.J.); polypropylene/Seprafilm®: Sepramesh® (Genzyme, Cambridge, Mass.), Sepramesh® IP (Genzyme, Cambridge, Mass.); polypropylene/Vicryl: Vypro™ (Ethicon, Somerville, N.J.), Vypro™ II (Ethicon, Somerville, N.J.); polypropylene/Monocryl(poliglecaprone): Ultrapro® (Ethicon, Somerville, N.J.); and polyester/collagen: Parietex® Composite (Sofradim, Trevoux, France).

II. Tissue Repair Composition Preparation

The biocompatible tissue repair composition provided herein is made by swelling ATM fragments in an acid solution to create a homogeneous suspension of swollen ATM particles and the suspension is dried to produce a collagen film or sponge-like structure. Typically, the volume occupied by swollen ATM fragments is increased relative to the volume occupied by the same mass of ATM fragments that have not been swollen. In some embodiments, the swelling can be carried out at mildly elevated temperatures. The ATM can be in the form of fragments, i.e., particles, fibers or threads. Prior to swelling, the ATM can be washed to remove any residual cryoprotectant. Solutions used for washing can be any physiologically compatible solution; highly suitable washing solutions are, for example, deionized or distilled water, or phosphate buffered saline (PBS)

The ATM can be swollen in any acid solution that maintains the ATM fragments as a homogeneous suspension, and that does not result in substantial irreversible denaturation of the collagen fibers in the ATM. As defined herein, a homogeneous suspension of ATM particles is one in which the ATM particles are uniformly distributed in a liquid medium and that does not contain particulates that are larger than about 1000µ in size, e.g., larger than about 950µ, about 975µ, about 1000µ, about 1025µ, about 1050µ, about 1075µ, about 1100µ or more. As used herein, "substantial irreversible denaturation" refers generally to the dissociation of collagen fibrils into their constituent subfibrils and/or collagen molecules, such that the collagen subfibrils and/or molecules are substantially unable to refold and reassemble into native collagen fibrils. As used herein, in collagen subfibrils and/or molecules that are "substantially unable to refold and reassemble into native collagen fibrils", not more than 30% (e.g., not more than: 25%; 20%; 15%; 10%; 5%; 2%; 1%; 0.1%; 0.01%; or less) of the collagen subfibrils and/or molecules are able refold and reassemble into native collagen fibrils. The native collagen fibril is a bundle of many subfibrils, each of which in turn is a bundle of microfibrils. A microfibril consists of helically coiled collagen molecules, each consisting of three helical polypeptide chains. This arrangement of the collagen molecules within the collagen fibrils results in a characteristic 64-67 nm banding periodicity. Typically, irreversibly denatured collagen fibrils lack, or substantially, lack the banding periodicity found in the native collagen fibril. Substantial irreversible denaturation of collagen fibrils can be monitored by any method known to those of skill in the art, including, for example, but not limited to, transmission electron microscopy, scanning electron microscopy, and atomic force microscopy or biochemical or enzymatic methods, e.g., polyacrylamide gel electrophoresis or susceptibility to enzymatic cleavage by collagenase, pepsin or proteinase K. Thus, the ATM may be swollen in any acid solution that does not result in a substantial loss of banding periodicity.

It will be appreciated that the type of acid, concentration of acid, the length of swelling time, and the swelling temperature may be adjusted to achieve optimal swelling of the ATM. For example, ATM from different sources, e.g., different mammalian species or different strains or breeds of the same species, may require different swelling conditions in order to achieve optimal swelling without substantial irreversible denaturation of the collagen fibrils in the ATM.

An acid is a molecule that acts as a proton donor and thus increases the $H^+$ concentration of a solution. Acids that readily give up protons to water are strong acids, while those with only a slight tendency to give up protons are weak acids. A useful index of the $H^+$ ion concentration in a solution is the pH scale; an aqueous solution with a pH of less than 7 is considered to be acidic. Thus, the ATM fragments can be swollen in any aqueous solution having a pH below 7.0, e.g., 6.9, 6.5, 6.2, 6.0. 5.5, 5.0, 4.5, 4.0, 3.5, 3.0, 2.8, 2.6, 2.4, 2.2, 2.0, 1.8, 1.6, 1.5, 1.4, 1.3, 1.2, 1.0 and below. The pH will preferably be below 3.0. "About" indicates that the pH can vary by up to 0.2 pH units above or below the recited value. Thus, a pH of "about" 3.0, can include, for example, pH 2.8, 2.85, 2.90, 2.95, 3.0, 3.05, 3.10, 3.15, or 3.20. Examples of useful acids include acetic acid, ascorbic acid, boric acid, carbonic acid, citric acid, hydrochloric acid, lactic acid, phosphoric acid, sulfuric acid, tannic acid and trichloroacetic acid. Any combination of two or more acids can also be used.

The specific concentration of acid will depend in part, upon the relative strength of the acid, with stronger acids, e.g., hydrochloric acid or sulfuric acid, requiring lower concentrations and weaker acids, e.g., acetic acid, citric acid and lactic acid, requiring higher concentrations. Thus, the concentration and lower pH limit for incubation will vary from acid to acid. In some embodiments, the acid is a volatile acid, i.e., an acid that readily evaporates at normal temperatures and pressures. Appropriate concentrations and pH's are those that do not result in substantial irreversible denaturation of the collagen fibers of the ATM (see above).

One highly suitable acid is acetic acid. Acetic acid can be used at concentrations in a range between about 25 mM and about 250 mM, e.g., 25, 50, 75, 100, 125, 150, 175, 200, 225, 250, 275, 300, 325, 350, 375, 400, 425, 450, 475, 500, 525, 550, 575, or 600 mM. Another suitable acid is hydrochloric acid (HCl). HCl can be used at concentrations in a range between about 25 mM and about 200 mM, e.g., 25, 40, 50, 60, 80, 100, 175, and 200 mM. "About" indicates that the acid concentration can vary by up to 10% above or below the recited value. Thus, an acetic acid concentration of "about" 50 mM can include, for example, 45 mM, 46 mM, 47 mM, 48 mM, 49 mM, 50 mM, 51 mM, 52 mM, 53 mM, 54 mM, or 55 mM.

The ATM can be swollen in acid for any period of time required to produce a homogeneous suspension of ATM fragments. The ATM can be swollen, for example, for about 0.5, 1.0, 1.5, 2.0, 2.5, 3.0, 3.5, 4.0, 4.5, 5.0, 5.5, 6.0, 7.0, 8.0, 9.0, 10.0, 11.0, 12.0, 14, 16, 18, 20, 22, 24, 26 or more hours. "About" indicates that the swelling time can vary by up to 0.2 hours above or below the recited value. Thus, a swelling time of "about" 3 hours can include, for example, 2.8 hours, 2.85 hours, 2.90 hours, 2.95 hours, 3.0 hours, 3.05 hours, 3.10 hours, 3.15 hours, or 3.20 hours.

The final concentration of ATM in the acid solution can be any concentration that swells uniformly and that results in a homogeneous suspension of ATM fragments. The swelling properties may vary according to the source of the tissue from which the ATM was derived; in general, useful concentrations (w/v) for porcine-derived ATM can range from about 0.1% e.g., 0.08%, 0.085%, 0.09%, 0.1%, 0.15% to about 4%, e.g., about 3.8%, 3.85%, 3.9%, 4.0%, 4.05%, 4.1%, 4.15%, or 4.2%. A suitable concentration for porcine-derived ATM is 0.5%. The extent of increase in volume of the ATM fragments can be measured by collecting the ATM fragments by centrifugation and determining the volume occupied by the pellets before and after the swelling period (see Example 1). The change in volume can be 1.2-fold, 1.5-fold, 2-fold, 3-fold, 4-fold, 5-fold, 6-fold, 7-fold or more relative to the ATM prior to acid swelling. The extent of the swelling will vary from ATM to ATM and from species to species. Generally, but not necessarily, conditions for swelling are used that result in maximal swelling of the ATM. After swelling, the ATM fragments will occupy a volume at least 1.2 times greater than they occupied prior to swelling. For example, the fragments can occupy a volume that is 1.2 times, 1.5 times, 1.8 times, 2.0 times, 3.0 times, 4.0 times, 5.0 times, 6.0 time, 7.0 times, 8.0 times, 9.0 times, 10.0 times, 11.0 times, 12.0 times or greater than the volume occupied prior to swelling. Any method in the art can be used to assay the extent of the swelling, including, for example, without limitation, direct measurement of the volume occupied by the ATM, or indirect measurements such as changes in density, viscosity or light scattering of the ATM solution.

The homogeneous suspension of the ATM fragments of the invention can be subjected to mildly elevated temperatures relative to ambient temperature. As defined herein, ambient temperature is from about 23° C. to about 27° C., e.g., 23° C., 24° C., 25° C., 26° C. or 27° C. As defined herein, "mildly elevated temperatures" include temperatures ranging from about 28° C. to about 44° C., e.g., 28° C., 29° C., 30° C., 31° C., 32° C., 33° C., 34° C., 35° C., 36° C., 37° C., 38° C., 39° C., 40° C., 41° C., 42° C., 43° C. or 44° C. The ATM can be subjected to mildly elevated temperatures either before the acid swelling step, at the same time as the acid swelling step, or after the acid swelling step. "About" indicates that the temperature can vary by up to 2° C. above or below the recited value. Thus, a temperature of "about" 30° C. can include, for example, 28.0° C., 28.5° C., 29.0° C., 2.95° C., 30.0° C., 30.5° C., 31° C., 31.5° C., or 32.0° C., The homogeneous suspension of the ATM fragments can be subjected to mildly elevated temperature for, for example, about 0.5, 1.0, 1.5, 2.0, 2.5, 3.0, 3.5, 4.0, 4.5, 5.0, 5.5, 6.0, 7.0, 8.0, 9.0, 10.0, 11.0, 12.0, 14, 16, 18, 20, 22, 24, 26 or more hours. "About" indicates that the swelling time can vary by up to 0.2 hours above or below the recited value. Thus, a swelling time of "about" 3 hours can include, for example, 2.8 hours, 2.85 hours, 2.90 hours, 2.95 hours, 3.0 hours, 3.05 hours, 3.10 hours, 3.15 hours, or 3.20 hours.

Once the ATM has been swollen in acid and subjected to elevated temperatures, it can be used to form either a biocompatible mesh composition or a biocompatible dermal film composition. To form the biocompatible mesh composition, the homogeneous ATM solution can be applied to a biocompatible mesh such that the woven mesh is impregnated with the solution. Any methods for coating mesh materials that retain the biocompatible properties of the coated mesh can be used. For example, swollen ATM can be poured or extruded into a container and the mesh materials added to and/or embedded in the ATM suspension. Alternatively or in addition, the swollen ATM can be deposited onto the mesh by aerosolization, spraying, centrifugation or filtration. Any container know to those in the art can be used, for example, a flat polypropylene or polystyrene dish. Alternatively, or in addition, the mesh materials can be placed in an appropriately sized container or mold and coated by pouring or extruding the swollen ATM onto the mesh. The coated mesh can then be dried and, optionally, the coating and drying process repeated one, two, three or more times.

In general, the mesh can be immersed in the ATM solution to a depth of about 0.5 to about 1.0 cm depending, in part, upon the extent of swelling of the ATM swells and the coating thickness desired. More specifically, the mesh can be coated with about 5 mg to about 10 mg dry weight of ATM per $cm^2$ of mesh. Thus, the mesh can be coated with 5.0, 5.5, 6.0, 6.5, 7.0, 7.5, 8.0, 8.5, 9.0, 9.5, or 10.0 mg of ATM per $cm^2$ of mesh. Depending upon how many times the coating process is repeated, the ATM coating on the mesh can be from about 0.1 to about 1.0 mm thick. The thickness of the coating may vary depending upon the intended application. Thus, thinner coatings may be more suitable for mesh that will be rolled up and inserted, for example, via a trochar, while thicker coatings may be used for mesh that will be applied directly to a tissue in need of repair. Biocompatible dermal films can be formed by drying the homogeneous ATM solution in an appropriate vessel to give a film-like or sponge-like sheet that can be removed from the vessel (see Example 2). Any vessel known to those in the art can be used, for example, a flat polypropylene or polystyrene dish. Alternatively, a contoured dish can be used to provide texture or functionality, for example, ribbing, ridging or corrugation, to the surface of the ATM coating. The ATM solution can be applied to a surface to a depth of about 0.5 to 1.0 mm. More specifically, about 5 mg to about 10 mg of ATM can be used per cm$^2$ of vessel surface area. Thus, the vessel can be coated with 5.0, 5.5, 6.0, 6.5, 7.0, 7.5, 8.0, 8.5, 9.0, 9.5, or 10.0 mg of ATM per cm$^2$.

The biocompatible tissue repair composition can be dried by any method known in the art that will result in the retention of biological and physical functions of the tissue repair composition. Drying methods include, without limitation, e.g., air drying, drying in atmosphere of, or under a stream of, inert gas (e.g., nitrogen or argon). The drying temperature may be ambient temperature, e.g., about 25° C. or it can be a temperature that is mildly elevated relative to ambient temperature, e.g., 28° C., 29° C., 30° C., 31° C., 32° C., 33° C., 37° C., 38° C., 39° C., 40° C., 41° C., 42° C., 43° C. or 44° C. Alternatively, the biocompatible tissue repair composition can be freeze-dried. Freeze-drying is a routine technique used in the art (see, for example, U.S. Pat. Nos. 4,619,257; 4,676,070; 4,799,361; 4,865,871; 4,964,280; 5,024,838; 5,044,165; 5,154,007; 6,194,136; 5,336,616; 5,364,756; and 5,780,295, the disclosures of all of which are incorporated herein by reference in their entirety) and suitable equipment is available from commercial sources such as Labconco (Kansas City, Mo., USA). Freeze-drying involves the removal of water or other solvent from a frozen product by a process called sublimation. Sublimation occurs when a frozen liquid (solid) goes directly to the gaseous state without passing through the liquid phase. Those skilled in the art are well aware of the different freeze-drying methodologies available in the art [see, e.g., "A Guide to Freeze-drying for the Laboratory"—an industry service publication by Labconco, (2004); and Franks (1994) Proc. Inst. Refrigeration. 91: 32-39]. Freeze-drying may be accomplished by any of a variety of methods, including, for example, the manifold, batch, or bulk methods.

In some embodiments, the molecules of the ATM (e.g., collagen molecules), with or without mesh substrates, can be chemically cross-linked (e.g. covalently linked) to themselves and/or, in the case of ATM-coated mesh substrates, to the mesh substrate. Chemical cross-linking agents can be homo-bifunctional (the same chemical reaction takes place at each end of the linker) or hetero-bifunctional (different chemical reactions take place at the ends of the linker). The chemistries available for such linking reactions include, but are not limited to, reactivity with sulfhydryl, amino, carboxyl, diol, aldehyde, ketone, or other reactive groups using electrophilic or nucleophilic chemistries, as well as photochemical cross-linkers using alkyl or aromatic azido or carbonyl radicals. Examples of chemical cross-linking agents include, without limitation, glutaraldehyde, carbodiimides, bisdiazobenzidine, and N-maleimidobenzoyl-N-hydroxysuccinimide ester. Chemical cross-linkers are widely available from commercial sources (e.g., Pierce Biotechnology (Rockford, Ill.); Invitrogen (Carlsbad, Calif.); Sigma-Aldrich (St. Louis, Mo.); and US Biological (Swampscott, Mass.)). Particularly suitable cross-linking reagents include 1-ethyl-3-[3-dimethylaminopropyl]carbodiimide hydrochloride (EDAC) and N-hydroxysulfosuccinimide (NHS).

Generally, cross-linking can be carried out by hydrating the dried coated mesh or dermal film directly in a solution of a cross-linking reagent. Alternatively, cross-linking reagents that are active at acidic pH can be added to acid swollen ATM before the ATM is poured over the mesh or applied directly to the substrate. The duration of the cross-linking reaction may vary according to the cross-linking agent that is used, reagent concentration, the source of the ATM, the type of mesh substrate, the reaction temperature and the tensile strength desired.

Optionally, the biocompatible tissue repair compositions can be submitted to treatments to diminish the bioburden. This process is expected to decrease the level of infectious microorganisms within the biocompatible tissue repair compositions. As used herein, a process used to inactivate or kill "substantially all" microorganisms (e.g., bacteria, fungi (including yeasts), and/or viruses) in the biocompatible tissue repair compositions is a process that reduces the level of microorganisms in the biocompatible tissue repair compositions by least 10-fold (e.g., at least: 100-fold; 1,000-fold; $10^4$-fold; $10^5$-fold; $10^6$-fold; $10^7$-fold; $10^8$-fold; $10^9$-fold; or even $10^{10}$-fold) compared to the level in the biocompatible tissue repair compositions prior to the process. Any standard assay method may be used to determine if the process was successful. These assays can include techniques that directly measure microbial growth, e.g., the culture of swab samples on artificial growth media, or molecular detection methods, such as quantitative PCR.

The biocompatible tissue repair compositions can be exposed to γ-, x-, e-beam, and/or ultra-violet (wavelength of 10 nm to 320 nm, e.g., 50 nm to 320 nm, 100 nm to 320 nm, 150 nm to 320 nm, 180 nm to 320 nm, or 200 nm to 300 nm) radiation in order to decrease the level of, or eliminate, viable bacteria and/or fungi and/or infectious viruses. More important than the dose of radiation that the biocompatible tissue repair compositions is exposed to is the dose absorbed by the biocompatible tissue repair compositions. While for thicker biocompatible tissue repair compositions, the dose absorbed and the exposure dose will generally be close, in thinner biocompatible tissue repair compositions the dose of exposure may be higher than the dose absorbed. In addition, if a particular dose of radiation is administered at a low dose rate over a long period of time (e.g., two to 12 hours), more radiation is absorbed than if it is administered at a high dose rate over a short period of time (e.g., 2 seconds to 30 minutes). One of skill in the art will know how to test for whether, for a particular biocompatible tissue repair compositions, the dose absorbed is significantly less than the dose to which the biocompatible tissue repair compositions is exposed and how to account for such a discrepancy in selecting an exposure dose. Appropriate absorbed doses of γ-, x-, or e-beam irradiation can be 6 kGy-45 kGy, e.g., 8 kGy-38 kGy, 10 kGy-36 kGy, 12 kGy-34 kGy. Thus, the dose of γ-, x-, and or e-beam irradiation can be, for example, 12, 13, 14, 15, 16, 17, 18, 19, 20, 21, 22, 23, 24, 25, 26, 27, 28, 29, 30, 31, 32, 33, or 34 kGy.

The biocompatible tissue repair composition components, the fragmented ATM and the biocompatible mesh, mixed or separated, can be irradiated (at any of the above doses) at any stage of the biocompatible tissue repair composition preparation. In addition, the irradiation of the biocompatible tissue repair composition can be the second or even third exposure of the components of the biocompatible tissue repair composition to irradiation. Thus, for example, the fragmented ATM and the biocompatible mesh can be irradiated separately, mixed to form the biocompatible mesh composition and then the biocompatible mesh composition can be irradiated.

Generally, the biocompatible tissue repair composition is rehydrated prior to grafting or implantation. Alternatively, the biocompatible tissue repair composition can be grafted or implanted without prior rehydration; in this case rehydration occurs in vivo. For rehydration, the biocompatible tissue repair composition can be incubated in any biologically compatible solution, for example, normal saline, phosphate-buffered saline, Ringer's lactate or standard cell culture medium. The biocompatible tissue repair composition is incubated in a solution for sufficient time for the biocompatible tissue repair composition to become fully hydrated or to regain substantially the same amount of water as the mixture from which the biocompatible tissue repair composition was made contains. Generally, the incubation time in the rehydration solution will be from about fifteen seconds to about one hour, e.g., about five minutes to about 45 minutes, or about 10 minutes to about 30 minutes. "About" indicates that the incubation time can vary by up to 20% above or below the recited value. Thus, an incubation time of "about" 30 minutes can include, for example, 24 minutes, 25 minutes, 26 minutes, 27 minutes, 28 minutes, 29 minutes, 30 minutes, 31 minutes, 32 minutes, 33 minutes, 34 minutes, 35 minutes, or 36 minutes. The rehydration solution can optionally be replaced with fresh solution as many times as desired. The temperature of the incubations will generally be ambient (e.g., room) temperature or can be at from about 15° C. to about 40° C., e.g., at about 20° C. to about 35° C. "About" indicates that the temperature can vary by up to 2° C. above or below the recited value. Thus, a temperature of "about" 30° C. can include, for example, 28.0° C., 28.5° C., 29.0° C., 2.95° C., 30.0° C., 30.5° C., 31.0° C., 31.5° C., or 32.0° C. The vessel containing the biocompatible tissue repair composition and rehydration solution can be agitated gently during the incubation if so desired. Following rehydration, the biocompatible tissue repair composition can be further shaped or trimmed into a form suitable for implantation at a particular site.

III. Tissue and Organ Repair

The biocompatible tissue repair compositions described herein can be used to treat any of a wide range of disorders in which amelioration or repair of tissue is needed. Tissue defects can arise from diverse medical conditions, including, for example, congenital malformations, traumatic injuries, infections, and oncologic resections. Thus, the biocompatible tissue repair compositions can be used to repair defects in any soft tissue, e.g., tissues that connect, support, or surround other structures and organs of the body. The biocompatible tissue repair compositions can also be used in support of bone repair, e.g., as a periosteal graft to support bone or an articular graft to drive cartilage repair. Soft tissue can be any non-osseous tissue. Soft tissue can also be epithelial tissue, which covers the outside of the body and lines the organs and cavities within the body. Examples of epithelial tissue include, but are not limited to, simple squamous epithelia, stratified squamous epithelia, cuboidal epithelia, or columnar epithelia.

Soft tissue can also be connective tissue, which functions to bind and support other tissues. One example of connective tissue is loose connective tissue (also known as areolar connective tissue). Loose connective tissue, which functions to bind epithelia to underlying tissues and to hold organs in place, is the most widely distributed connective tissue type in vertebrates. It can be found in the skin beneath the dermis layer; in places that connect epithelium to other tissues; underneath the epithelial tissue of all the body systems that have external openings; within the mucus membranes of the digestive, respiratory, reproductive, and urinary systems; and surrounding the blood vessels and nerves. Loose connective tissue is named for the loose "weave" of its constituent fibers which include collagenous fibers, elastic fibers (long, thread-like stretchable fibers composed of the protein elastin) and reticular fibers (branched fibers consisting of one or more types of very thin collagen fibers). Connective tissue can also be fibrous connective tissue, such as tendons, which attach muscles to bone, and ligaments, which joint bones together at the joints. Fibrous connective tissue is composed primarily of tightly packed collagenous fibers, an arrangement that maximizes tensile strength. Soft tissue can also be muscle tissue. Muscle tissue includes: skeletal muscle, which is responsible for voluntary movements; smooth muscle, which is found in the walls of the digestive tract, bladder arteries and other internal organs; and cardiac muscle, which forms the contractile wall of the heart.

The biocompatible tissue repair compositions can be used to repair soft tissues in many different organ systems that fulfill a range of physiological functions in the body. These organ systems can include, but are not limited to, the muscular system, the genitourinary system, the gastroenterological system, the integumentary system, the circulatory system and the respiratory system. The compositions are particularly useful for repairs to connective tissue, including the fascia, a specialized layer that surrounds muscles, bones and joints, of the chest and abdominal wall and for repair and reinforcement of tissue weaknesses in urological, gynecological and gastroenterological anatomy.

The biocompatible tissue repair compositions are highly suitable for hernia repair. A hernia is the protrusion of the contents of a body cavity out of the body cavity in which the contents are normally found. These contents are often enclosed in the thin membrane that lines the inside of the body cavity; together the membrane and contents are referred to as a "hernial sac". Most commonly hernias develop in the abdomen, when a weakness in the abdominal wall expands into a localized hole or defect through which the intestinal protrusion occurs. These weaknesses in the abdominal wall typically occur in locations of natural thinning of the abdominal wall, that is, at sites where there are natural openings to allow the passage of canals for the blood vessels that extend from the abdomen to the extremities and other organs. Other areas of potential weakness are sites of any previous abdominal surgery. Fatty tissue usually enters a hernia first, but it can be followed by a segment of intestine or other intraabdominal organ. If a segment of internal organ becomes trapped within the hernia sac such that the blood supply to the organ is impaired, the patient is at risk for serious complications including intestinal blockage, gangrene, and death. Hernias do not heal spontaneously and often increase in size over time, so that surgical repair is necessary to correct the condition. In general, hernias are repaired by reinserting the hernia sac back into the body cavity followed by repair of the weakened muscle tissue.

There are many kinds of hernias. With the exception of inguinal and scrotal hernias, which are only present in males, hernias can be found in individuals of any age or gender. Examples of hernias include: direct inguinal hernias, in which the intestine can bulge into the inguinal canal via the back wall of the inguinal canal; indirect inguinal hernias, in which the intestine can bulge into the inguinal canal via a weakness at the apex of the inguinal canal; fermoral hernias, in which the abdominal contents pass into the weak area created by the passage of the femoral blood vessels into the lower extremities; scrotal hernias, in which the intestinal contents bulge into the scrotum; Spigelian hernia, in which the hernia occurs along the edge of the rectus abdominus muscle; obturator hernia, in which the abdominal contents (e.g., intestine or other abdominal organs) protrude into the obturator canal, lumbar hernias, e.g., Petit's hernia, in which the hernia is through Petit's triangle, the inferior lumbar triangle, and Grynfeltt's hernia, in which the hernia is through Grynfeltt-Lesshaft triangle, the superior lumbar triangle; Richter's hernia, in which only one sidewall of the bowel becomes strangulated; Hesselbach's hernia, in which the hernia is through Hesselbach's triangle; pantaloon hernia, in which the hernia sac protrudes on either side of the inferior epigastric vessels to give a combined direct and indirect inguinal hernia; Cooper's hernia; epigastric hernia (in which the hernia occurs between the navel and the lower part of the rib cage in the midline of the abdomen); diaphragmatic or hiatal hernias, e.g., Bochdalek's hernia and Morgagni's hernia, in which a portion of the stomach protrudes through the diaphragmatic esophageal hiatus; and umbilical hernia, in which the protrusion is through the navel.

In contrast to hernias of congenital origin, incisional hernias, also known as ventral or recurrent hernias, occur in the abdomen in the area of an old surgical scar. Incisional hernias have a higher risk of returning after surgical repair than do congenital hernias. Moreover, in the case of multiple recurrent hernias, i.e., hernias that recur after two or more repairs have been carried out, the likelihood of successful repair decreases with each subsequent procedure.

The biocompatible tissue repair compositions can be used to treat other medical conditions that result from tissue weakness. One condition for which the biocompatible tissue repair compositions are useful is in the repair of organ prolapse. Prolapse is a condition in which an organ, or part of an organ, falls or slips out of place. Prolapse typically results from tissue weakness that can stem from either congenital factors, trauma or disease. Pelvic organ prolapse can include prolapse of one or more organs within the pelvic girdle; tissue weakening due to pregnancy, labor and childbirth is a common cause of the condition in women. Examples of organs involved in pelvic organ prolapse include the bladder (cytocele), which can prolapse into the vagina; the urethra, which can prolapse into the vagina; the uterus, which can prolapse into the vagina; the small intestine (enterocele), which can prolapse against the wall of the vagina; the rectum (rectocele), which can prolapse against the wall of the vagina; and vaginal prolapse, in which a portion of the vaginal canal can protrude from the opening of the vagina. Depending upon the organ involved and the severity of the prolapse, patients with pelvic organ prolapse may experience pain upon sexual intercourse, urinary frequency, urinary incontinence, urinary tract infection, renal damage, and constipation. Remedies include both non-surgical and surgical options; in severe cases, reconstruction of the tissues of the pelvic floor, i.e., the muscle fibers and connective tissue that span the area underneath the pelvis and provides support for the pelvic organs, e.g., the bladder, lower intestines, and the uterus (in women) may be required.

The biocompatible tissue repair compositions are also useful in repairs of the gastrointestinal system. Esophageal conditions in need of repair include, but are not limited to, traumatic rupture of the esophagus, e.g., Boerhaave syndrome, Mallory-Weiss syndrome, trauma associated with iatrogenic esophageal perforation that may occur as a complication of an endoscopic procedure or insertion of a feeding tube or unrelated surgery; repair of congenital esophageal defects, e.g., esophageal atresia; and oncologic esophageal resection.

The biocompatible tissue repair compositions can be used to repair tissues that have never been repaired before or they can be used to repair tissues that have been treated one or more times with biocompatible tissue repair compositions or with other methods known in the art or they can be used along with other methods of tissue repair including suturing, tissue grafting, or synthetic tissue repair materials.

The biocompatible tissue repair compositions can be applied to an individual in need of treatment using techniques known to those of skill in the art. The biocompatible tissue repair compositions can be: (a) wrapped around a tissue that is damaged or that contains a defect; (b) placed on the surface of a tissue that is damaged or has a defect; (c) rolled up and inserted into a cavity, gap, or space in the tissue. One or more (e.g., one, two, three, four, five, six, seven, eight, nine, ten, 12, 14, 16, 18, 20, 25, 30, or more) such biocompatible tissue repair compositions, stacked or adjacent to each other, can be used at any particular site. The biocompatible tissue repair compositions can be held in place by, for example, sutures, staples, tacks, or tissue glues or sealants known in the art. Alternatively, if, for example, packed sufficiently tightly into a defect or cavity, they may need no securing device.

Therapeutic Agents

Therapeutic agents that aid tissue regeneration can be included in the biocompatible tissue repair compositions. These agents can include cells, growth factors or small molecule therapeutics. These agents can be incorporated into the biocompatible tissue repair compositions prior to the biocompatible tissue repair compositions being placed in the subject. Alternatively, they can be injected into the biocompatible tissue repair composition already in place in a subject. These agents can be administered singly or in combination. For example, a biocompatible tissue repair composition can be used to deliver cells, growth factors and small molecule therapeutics concurrently, or to deliver cells plus growth factors, or cells plus small molecule therapeutics, or growth factors plus small molecule therapeutics.

Naturally, administration of the agents mentioned above can be single, or multiple (e.g., two, three, four, five, six, seven, eight, nine, 10, 15, 20, 25, 30, 35, 40, 50, 60, 80, 90, 100, or as many as needed). Where multiple, the administrations can be at time intervals readily determinable by one skilled in art. Doses of the various substances and factors will vary greatly according to the species, age, weight, size, and sex of the subject and are also readily determinable by a skilled artisan.

Histocompatible, viable cells can be restored to the biocompatible tissue repair compositions to produce a permanently accepted graft that may be remodeled by the host. Cells can be derived from the intended recipient or an allogeneic donor. Cell types with which the biocompatible tissue repair compositions can be repopulated include, but are not limited to, embryonic stem cells (ESC), adult or embryonic mesenchymal stem cells (MSC), monocytes, hematopoetic stem cells, gingival epithelial cells, endothelial cells, fibroblasts, or periodontal ligament stem cells, prochondroblasts, chondroblasts, chondrocytes, pro-osteoblasts, osteocytes, or osteoclasts. Any combination of two or more of these cell types (e.g., two, three, four, five, six, seven, eight, nine, or ten) may be used to repopulate the biocompatible tissue repair composition. Methods for isolating specific cell types are well-known in the art. Donor cells may be used directly after harvest or they can be cultured in vitro using standard tissue culture techniques. Donor cells can be infused or injected into the biocompatible tissue repair composition in situ just prior to placing of the biocompatible tissue repair composition in a mammalian subject. Donor cells can also be cocultured with the biocompatible tissue repair composition using standard tissue culture methods known to those in the art.

Growth factors that can be incorporated into the biocompatible tissue repair composition include any of a wide range of cell growth factors, angiogenic factors, differentiation factors, cytokines, hormones, and chemokines known in the art. Growth factors can be polypeptides that include the entire amino acid sequence of a growth factor, a peptide that corresponds to only a segment of the amino acid sequence of the native growth factor, or a peptide that derived from the native sequence that retains the bioactive properties of the native growth factor. Any combination of two or more of the factors can be administered to a subject by any of the means recited below. Examples of relevant factors include vascular endothelial cell growth factors (VEGF) (e.g., VEGF A, B, C, D, and E), platelet-derived growth factor (PDGF), insulin-like growth factor (IGF) I and IGF-II, interferons (IFN) (e.g., IFN-α, β, or γ), fibroblast growth factors (FGF) (e.g., FGF1-10), epidermal growth factor, keratinocyte growth factor, transforming growth factors (TGF) (e.g., TGFα or β), tumor necrosis factor-α, an interleukin (IL) (e.g., IL-1-IL-18), Osterix, Hedgehogs (e.g., sonic or desert), SOX9, bone morphogenetic proteins (BMP's), in particular, BMP 2, 4, 6, and 7 (BMP-7 is also called OP-1), parathyroid hormone, calcitonin prostaglandins, or ascorbic acid.

Factors that are proteins can also be delivered to a recipient subject by administering to the subject: (a) expression vectors (e.g., plasmids or viral vectors) containing nucleic acid sequences encoding any one or more of the above factors that are proteins; or (b) cells that have been transfected or transduced (stably or transiently) with such expression vectors. Such transfected or transduced cells will preferably be derived from, or histocompatible with, the recipient. However, it is possible that only short exposure to the factor is required and thus histo-incompatible cells can also be used.

Small molecule drugs can also be incorporated into the biocompatible tissue repair composition, thus facilitating localized drug delivery. Recurrent hernias can be refractory to repair, due, in some instances, to indolent bacterial colonization that weakens the repair site and retards healing. Long-term systemic administration of antibiotics may only be partially effective against such subclinical infections. Incorporation of antimicrobial agents into the biocompatible tissue repair composition can provide local high concentrations of antibiotics, thus minimizing the risk of adverse effects associated with long term high systemic doses. An antimicrobial agent can be an antibiotic. Examples of antibiotics include, without limitation, any representative classes of antibiotics, e.g., 1) aminoglycosides, such as gentamycin, kanamycin, neomycin, streptomycin or tobramycin; 2) cephalosporins, such as cefaclor, cefadroxil or cefotaxime; 3) macrolides, such as azithromycin, clarithromycin, or erythromycin; 4) penicillins, such as amoxicillin, carbenicillin or penicillin; 5) peptides, such as bacitracin, polymixin B or vancomycin; 6) quinolones, such as ciprofloxacin, levofloxacin, or enoxacin; 7) sulfonamides, such as sulfamethazole, sulfacetimide; or sulfamethoxazole; 8) tetracyclines, such as doxycycline, minocycline or tetracycline; 8) other antibiotics with diverse mechanisms of action such as rifampin, chloramphenicol, or nitrofuratoin. Other antimicrobial agents, e.g., antifungal agents and antiviral agents can also be included in the biocompatible tissue repair compositions.

Chemotherapeutic agents can also be included in the biocompatible tissue repair compositions. Malignant tumors that occur in soft tissue, including for example, tumors of the esophagus, stomach, colon, bladder are typically treated by tumor resection and systemic administration of anticancer drugs. Incorporation of anticancer agents into the biocompatible tissue repair compositions can provide local high concentrations of chemotherapy, thus mitigating the toxicity associated with long term high systemic doses. Examples of classes of chemotherapeutic agents include, without limitation, 1) alkylating agents, e.g., cyclophosphamide; 2) anthracyclines, e.g., daunorubicin, doxorubicin; 3) cycloskeletal disruptors, e.g., paclitaxel; 4) topoisomerase inhibitors, e.g., etoposide; 5) nucleotide analogues, e.g., azacitidine, fluorouracil, gemcitabine; 6) peptides, e.g., bleomycin; 7) platinum-based agents, e.g., carboplatin, cisplatin; 8) retinoids, e.g., all-trans retinoic acid; and 9) vinca alkaloids, e.g., vinblastine or vincristine.

IV. Articles of Manufacture

The biocompatible tissue repair compositions provided herein can be included in an article of manufacture or as a kit. In one embodiment, the kit can include the biocompatible tissue repair composition, packaging material, or a package insert, comprising instructions for a method of treatment. The packaging material can include components that promote the long term stability and sterility of the biocompatible tissue repair composition.

A number of embodiments of the invention have been described. Nevertheless, it will be understood that various modifications may be made without departing from the spirit and scope of the invention. Accordingly, other embodiments are within the scope of the following claims.

EXAMPLES

Example 1

Methods and Materials

Preparation of Acellular Tissue Matrix (ATM).

ATM was prepared from porcine dermal tissue procured from Yucatan Mini-Pigs. Porcine dermal tissue was processed according to standard LifeCell protocols as follows. Tissue was incubated in RPMI 1640 media containing 20 mM EDTA for 24 hours at 4° C. Skin epidermis was removed by incubating the tissue sample with gentle agitation in a de-epidermizing solution (phosphate-buffered saline (PBS), 10 mM EDTA, 0.5% Triton X-100, with lincomycin, vancomycin, polymyxin B and cefoxitin) for 22.5 hours at room temperature. The epidermal layer was then physically removed from dermis. The epidermis was discarded and the dermis was subjected to further processing. Cellular components and debris were removed by rinsing the dermis in decellularizing solution (10 mM HEPES, pH 8.0, 10 mM EDTA, 2% sodium deoxycholate) for 15 minutes, followed by gentle agitation in a fresh lot of decellularizing solution for 18 hours at room temperature. The dermis was then incubated in DNAse solution (20 mM HEPES, pH 7.2, 20 mM calcium chloride, 20 mM magnesium chloride, and 1 U/ml DNase (Pulmozyme®, Genentech, South San Francisco, Calif.), followed by washing in PBS, 10 mM EDTA, pH 7.2. The DNase-treated dermis was then incubated in pre-freeze solution and freeze dried to produce the ATM in sheet form (XenoDerm™). The XenoDerm™ was micronized using a Spex-Certiprep Freeze Mill. The approximate particle size of the micronized XenoDerm™ was between about 100 and 200μ. The micronized material was used as the starting material for preparation of the coated mesh and dermal films as described in the examples below.

Determination of Cryoprotectant Content of Micronized Porcine Dermis.

100 mg of micronized tissue was washed 3 times with water to remove soluble cryoprotectant. The washed material was then freeze-dried and weighed. It was determined that the micronized porcine dermis consisted of approximately 50% cryoprotectant and 50% acellular tissue matrix (ATM).

Swelling of ATM in Acetic Acid.

A useful acetic acid concentration for swelling of regenerative tissue matrix (ATM) was empirically determined. 50 mg of micronized porcine dermis, containing 26 mg ATM, was washed 3 times with water, then suspended in 5 mL of acetic acid at the concentrations indicated in Table 1. The ATM samples were incubated for 3 hours at room temperature with occasional mixing. The swollen ATM particles were allowed to settle, the volume occupied by the swollen ATM was recorded; then the samples were subjected to low speed centrifugation and the packed volume of the ATM pellets was recorded. 100 mM acetic acid (pH at about 2.6) yielded almost maximal swelling of the ATM, i.e., the magnitude of the difference between swollen and packed volume, as assessed either by gravity or centrifugation (Table 1). At lower concentrations of acetic acid, the ATM swelling was non-uniform, producing a non-homogeneous suspension with large particulates. Attempts to increase the ATM concentration to greater than 0.5% ATM (w/v) resulted in the formation of a non-homogenous suspension containing numerous particulates that were not dissipated either by adding salt (10 mM sodium chloride) or increasing the pH (>3.0).

TABLE 1

Swelling of ATM in acetic acid

| Acetic acid (mM) | Swollen ATM volume (ml) | Packed ATM volume (ml) |
| --- | --- | --- |
| 0 | 0.4 | 0.4 |
| 25 | 3.0 | 2.2 |
| 50 | 3.6 | 2.6 |
| 100 | 4.3 | 2.7 |
| 250 | 4.8 | 3.0 |

The integrity of the collagen fibers in the acid swollen ATM was evaluated by transmission electron microscopy (TEM). Samples of micronized human dermis (Cymetra™) were rehydrated in 50, 100, 250 or 500 mM acetic acid. Acid was removed by washing in 0.9% saline and the samples prepared for transmission electron microscopy. Collagen periodicity was observed in individual collagen fibers from all samples analyzed with no apparent differences in the banding pattern or fiber size. An increase in the separation of the collagen fibers that appeared proportional to the concentration of acetic acid used to rehydrate the Cymetra™ was noted.

Example 2

Preparation and Comparison of Film-Coated and Sponge-Coated Polypropylene Mesh

The initial steps in the preparation of the film-coated and sponge-coated mesh were identical. Briefly, the ATM was swollen in acid and poured over polypropylene mesh. Drying the coated mesh in a nitrogen/air atmosphere produced a uniformly coated mesh, about 0.5 mm in thickness, that resembled cellophane; this material is referred to as "film-coated mesh". In contrast, freeze-drying the coated mesh, resulted in material with a loose consistency, of about 2-3 mm in thickness, resembling a cotton-ball; this material is referred to as "sponge-coated mesh".

Preparation of Film-Coated Polypropylene Mesh.

ATM (2.5 mg ATM/$cm^2$ of polypropylene mesh) was washed 3 times in water to remove residual cryoprotectant and salts, then swollen in 100 mM acetic acid at a final concentration of 0.5% ATM for 3 hours at room temperature. Polypropylene mesh (PROLENE mesh, Ethicon, Inc.) was cut into pieces of about 7.5 cm×2.5 cm and each piece was placed individually in a single well (8 cm×3 cm) of a 4-well polystyrene dish (Nunc, catalog #267061). The acid swollen ATM was poured over the mesh to a depth of about 5 mm and the dish was incubated overnight in a nitrogen atmosphere. The dried film-coated mesh was lifted from the dish, hydrated for 15 minutes in 100 mM acetic acid, inverted and transferred to a clean polystyrene container. Freshly prepared acid swollen ATM was again poured over the film-coated mesh, which was then dried overnight in a nitrogen atmosphere. The dried double coated mesh was then removed from the polystyrene container.

In some instances, the ATM film-coated mesh was submitted to a cross-linking procedure. The dried, coated mesh was incubated for 3 hours at room temperature in 100 mM 4-morpholinoethanesulfonic acid (MES), pH 5.4, 20 mM 1-ethyl-3-[3-dimethylaminopropyl]carbodiimide hydrochloride (EDAC), 10 mM N-hydroxysulfosuccinimide (NHS) and 0.5 µM lysine. Cross-linked mesh was rinsed in saline and kept hydrated prior to in vitro or in vivo analysis.

Preparation of Sponge-Coated Polypropylene Mesh.

ATM (2.5 mg ATM/$cm^2$ of polypropylene mesh) was washed 3 times in water to remove residual cryoprotectant and salts, then swollen in 100 mM acetic acid at a final concentration of 5% ATM for 3 hours at room temperature. Polypropylene mesh (PROLENE mesh, Ethicon, Inc.) was cut into pieces of about 7.5 cm×2.5 cm and each piece was placed individually in a single well (8 cm×3 cm) of a 4-well polystyrene dish (Nunc, catalog #267061). The acid-swollen ATM was poured over the mesh (2.5 mg ATM/$cm^2$ of mesh) to a depth of about 5 mm. The acid-swollen ATM was poured over the mesh which was then freeze-dried. The dried sponge-coated polypropylene mesh was then removed from the polystyrene container.

In some instances, the ATM sponge-coated mesh was submitted to a cross-linking procedure. The dried, coated mesh was incubated for 3 hours at room temperature in 100 mM 4-morpholinoethanesulfonic acid (MES), pH 5.4, 20 mM 1-ethyl-3-[3-dimethylaminopropyl]carbodiimide hydrochloride (EDAC), 10 mM N-hydroxysulfosuccinimide (NHS) and 0.5 µM lysine. Cross-linked mesh was rinsed in saline and kept hydrated prior to in vitro or in vivo analysis.

The acid swollen ATM formed uniform films and sponges when dried. When rehydrated with physiological buffers, the films and sponges remained intact and maintained their original shape. Without acid treatment, dried micronized tissue failed to maintain shape when hydrated. Biomechanically, the films were stronger (both by touch and quantifiable testing) relative to the sponges.

Tensile Strength of Films and Sponges.

Films and sponges were prepared exactly as described in the methods above except that the polypropylene mesh was omitted from the samples. Films and sponges were rehydrated and their tensile strength was evaluated using an Instron 5865 testing machine (Instron Corporation, Norwood, Mass.) according to the manufacturer's specification. The results of this experiment are shown in Table 2, below. The values represent the mean maximum stress of two separate samples. The cross-linked films had the greatest overall strength and tolerated approximately 20-25% of the maximum stress tolerated by normal freeze dried ATM (Xenoderm™).

TABLE 2

Tensile strength of dermal films and sponges

| Sample | Cross-linking | Maximum Stress (MPa) |
| --- | --- | --- |
| Film | No | 0.07 |
| Sponge | No | 0.02 |
| Film | Yes | 4.05 |
| Sponge | Yes | 0.09 |
| normal sheet XenoDerm ™ | No | 15-20 |

Extracellular Matrix Denaturation Temperature of Films and Sponges.

The potential for the acid swollen ATM to remain stable under physiological conditions was also evaluated by in vitro methods, including, for example, measuring the denaturation temperature of the extracellular matrix, and the collagenase sensitivity of the acid swollen ATM. The denaturation temperature of the extracellular matrix was evaluated by differential scanning calorimetry (DSC). Hydrated samples were placed into high volume DSC pans, sealed and run in a DSC Q100 (TA Instruments) using an equilibration temperature of 2° C. with a ramp of 2.5° C./minute to 95° C. Films and sponges were prepared exactly as described in the methods above except that the polypropylene mesh was omitted from the samples. As indicated in Table 3, cross-linking appeared to increase the temperature required to denature the collagen matrix. In contrast, the denaturation temperatures of the non-cross-linked films and sponges were slightly less than that of the micronized porcine dermis from which they were made, indicating that the overall structural organization of collagen in the films and sponges was similar to that of native collagen. Moreover, the denaturation temperature of the films and sponges was higher than the normal mammalian body temperature of 37° C., indicating that the films and sponges would be stable at physiological temperatures.

TABLE 3

Denaturation temperature of dermal films and sponges

| Sample | Cross-linking | Denaturation Temperature (° C.) |
| --- | --- | --- |
| Film | No | 57 |
| Sponge | No | 57 |
| Film | Yes | 70 |
| Sponge | Yes | 70 |
| Micronized porcine dermis | No | 64 |

Histological Analysis of Film—and Sponge-Coated Polypropylene Mesh.

Film and sponge-coated polypropylene mesh samples were prepared as described above, then sectioned and stained with hemotoxylin and eosin (H&E). Dense eosinophilic material surrounded the polypropylene mesh in the film-coated mesh samples; in contrast, a loose network of eosinophilic material surrounded the polypropylene mesh in the sponge-coated mesh samples. Collagen bundles, typically found in the dermal matrix, were not observed in either the film or sponge-coated polypropylene mesh samples, although there were histologic artifacts associated with paraffin embedding of the mesh, suggesting the need for embedding in plastic prior to sectioning.

Example 3

Biocompatibility of Film- and Sponge-Coated Polypropylene Mesh

Biocompatibility of film- and sponge-coated mesh was evaluated in vivo in a time course experiment using an immune competent rat model. Film- and sponge-coated mesh samples, prepared with and without crosslinking, as described in Example 2, were implanted subdermally and removed for analysis at 1, 3, and 5 weeks after implantation. Control samples included uncoated polypropylene mesh and sheet Xenoderm™. Three replicates of each test article were implanted for each time point. Implants were inserted into small subdermal pockets (4 per rat) created on the dorsal surface of the animals. Following insertion of the test articles, wounds were closed with surgical staples.

Qualitative histological analysis of the explants was performed to evaluate cellular repopulation, vascularization, inflammation and persistence of the implanted extracellular matrix. Cellular repopulation and vascularization were assessed by evaluation of hematoxylin and eosin histological sections; inflammation was evidenced by the presence of cells with round densely stained nuclei; persistence of the extracellular matrix was evidenced by a uniform pinkish eosinophilic staining characteristic of cell cytoplasm and extracellular matrix proteins.

Histological analyses indicated that the control uncoated polypropylene mesh samples showed a dense, inflammatory fibrotic response at 1 week post-implantation that diminished only slightly after 3 and 5 weeks post implantation. The positive control, sheet XenoDerm™, which as described above, lacks a polypropylene mesh component, showed a relatively minor inflammatory response at the site of implantation, with an increased repopulation over the course of the 5 week time period. Both the sponge-coated polypropylene mesh and the cross-linked sponge-coated polypropylene mesh were fragile and tended to fall apart during the implantation procedure. Inflammatory responses, similar to that observed for the uncoated polypropylene mesh control samples, were noted for both the non-cross-linked and the cross-linked sponge samples, although small areas of extracellular matrix were still present in the latter at five weeks post-implantation. Mild inflammation was observed for both the film-coated polypropylene mesh and the cross-linked film-coated polypropylene mesh samples. However, persistence of extracellular matrix, as well as cellular repopulation was noted for the film-coated polypropylene mesh samples over the 5 week time-course, while no evidence of cellular repopulation was observed for the film-coated cross-linked polypropylene mesh samples. Thus, the film-coated mesh preparations showed the greatest degree of biocompatibility based on persistence of the ATM, a relatively low level of inflammation, and the capacity to repopulate and revascularize.

Example 4

Preparation of Polypropylene Mesh and Dermal Films Using a Thermal Drying Method The film-coated polypropylene mesh used in Examples 7, 10 and 11 and the dermal films used in Examples 5, 6, 7, 8, and 9 were made as follows.

Preparation of Film-Coated Polypropylene Mesh.

Freeze-dried sheet XenoDerm™ was micronized according the method described above. ATM was washed in water to remove residual cryoprotectant and salts, then swollen in 100 mM acetic acid at a final concentration of 0.5% ATM for 3 hours. The swelling temperatures ranged from 32-40° C. as detailed in the specific examples below. The acid-swollen ATM was poured into a polystyrene dish and the polypropylene mesh (7.5 cm×2.5 cm pieces) was immersed in the ATM solution to a depth of about 1 cm; 0.75 mg acid swollen ATM was used per $cm^2$ of polypropylene mesh. The polypropylene mesh was coated only once. Samples were dried as indicated below in Examples 7, 10 and 11.

Preparation of Dermal Films.

Dermal films, which did not contain polypropylene mesh, were prepared as follows. Freeze-dried sheet XenoDerm™ was micronized according the method described above. ATM was washed in water to remove residual cryoprotectant and salts, then swollen in 100 mM acetic acid at a final concentration of 0.5% ATM for 3 hours. The swelling temperatures ranged from 32-40° C. as detailed in the specific examples below. The acid-swollen ATM solution was poured into a polystyrene dish to a depth of about 0.5 cm; 0.75 mg acid swollen ATM was used per cm² of the polystyrene dish. Samples were dried as indicated below in Examples 5, 6, 8, and 9.

Example 5

Extracellular Matrix Denaturation Temperature of Dermal Films

Dermal films were prepared as described in Example 4 above using ATM that had been swollen at ambient temperature; films were dried in a nitrogen environment at either room temperature or on a heating block at 33° C., 37° C., or 43° C. Films that had been prepared using the cross-linking method described in Example 3, above, were included as a positive control. The denaturation profiles of the extracellular matrix of the resulting materials was evaluated by differential scanning calorimetry (DSC). As indicated in Table 5, the denaturation temperatures of the films dried at 33° C. and 37° C. were similar to those of control films that had been dried at room temperature, while the denaturation temperature of films dried at 43° C. was reduced relative to control films. Cross-linking appeared to increase the temperature required to denature the collagen matrix. These data suggested that because the denaturation temperature of the films was higher than the normal mammalian body temperature of 37° C., the films would be stable at physiological temperatures.

TABLE 5

Thermal denaturation of dermal films

| Drying temperature (° C.) | Cross-linking | Denaturation Temperature (° C.) |
| --- | --- | --- |
| Room temperature | No | 53 |
| 33 | No | 55 |
| 37 | No | 55 |
| 43 | No | 50 |
| room temperature | Yes | 72 |

Example 6

Collagenase Sensitivity of Dermal Films

The potential for the ATM coating to persist under physiological conditions was also evaluated by measuring the collagenase sensitivity of dermal films. Optimally, the ATM coating should persist long enough to permit cellular repopulation of the matrix, while still retaining enough of the native collagen structure to permit normal collagen turnover. Dermal films were prepared as described in Example 4 above using ATM that had been swollen at ambient temperature dried in a nitrogen environment at either room temperature or on a heating block at 33° C., 37° C. and 43° C. Films that had been prepared using the cross-linking method described in Example 3, above, were included as positive controls. Samples were digested with collagenase and the percent of collagen remaining in each sample, relative to the undigested sample, was assayed after 1, 2, 4, 6, and 24 hours of collagenase treatment. For collagenase digestion, 15-20 mg of dried film was placed in an eppendorf tube. Each sample was hydrated in 1 ml of 10 mM Tris, pH 7.4, 5 mM CaCl₂, followed by the addition of 0.25 mg of collagenase (25 µl of a 10 mg/ml solution) and incubated at 37° C. At the indicated time points, samples were cooled in ice and insoluble (non-digested) material was collected by centrifugation. Pellets were then dried and weighed to determine the percentage of remaining tissue. As indicated in Table 6, the cross-linked films were almost completely resistant to collagenase degradation. Films dried at elevated temperatures appeared to be slightly more susceptible to collagenase than those dried at room temperature. The apparent increase in material in some of the later timepoints in some of the samples reflects variability in the residual moisture content of the small sample sizes. These data indicated that the collagen in the dermal films was accessible to collagenase and was not irreversibly denatured, suggesting that the collagen fibrils within the ATM coated mesh would be subjected to normal physiological collagen turnover.

TABLE 6

Collagenase sensitivity of dermal films: percent collagen remaining over time.

| Collagenase digestion time (Hours) | Sample Drying Temperature (° C.) | | | | Room temperature, cross linked |
| --- | --- | --- | --- | --- | --- |
| | Room temperature | 33 | 37 | 43 | |
| 1 | 64% | 30% | 45% | 8% | 90% |
| 2 | 25% | 12% | 18% | 5% | 92% |
| 4 | 15% | 10% | 15% | 10%* | 93% |
| 6 | 10% | 20%* | 18%* | 20%* | 92% |
| 24 | 0% | 2% | 0% | 15%* | 80% |

Percentages refer to percentages of collagen remaining in sample after collagenase treatment.

Example 7

Biocompatibility of Coated Mesh: Evaluation in a Subdermal Immune Competent Rat Model The effect of preparation temperature on the biocompatibility of coated mesh samples was evaluated in a subdermal immune competent rat model. In brief, the swelling temperature of the ATM and the drying temperature of the coated mesh was systematically varied according the conditions in Table 7, below. The coated mesh samples were implanted, and the implants removed and evaluated histologically at intervals of 1, 3 and 5 weeks post-implantation.

The experimental groups were designated A through F and were subject to the following conditions. Samples B-F were immersed in the relevant swollen ATM fragment suspension and then treated as follows. Samples C and D were prepared from ATM that had been swollen in 0.1M acetic acid at room temperature. After coating, sample C was dried at 37° C. and sample D was dried at 40° C. Sample E was prepared from ATM that had been swollen in 0.1M acetic acid at 37° C.; sample F was prepared from ATM that had been swollen in 0.1M acetic acid at 40° C. Both samples E and F were dried at room temperature. Sample B was prepared from ATM that had been swollen in 0.1M acetic acid at room temperature, coated at room temperature and then dried at room temperature. Sample A, a control for factors related to coating in general, was uncoated polypropylene mesh. All samples were dried in a nitrogen atmosphere.

TABLE 7

Biocompatibility Study Experimental Design

| Sample | Polypropylenemesh | Swelling temperature (° C.) | Drying temperature (° C.) |
| --- | --- | --- | --- |
| A | Uncoated | not applicable | not applicable |
| B | Coated | RT[a] | RT[a] |
| C | coated | RT[a] | 37° |
| D | coated | RT[a] | 40° |
| E | coated | 37° | RT[a] |
| F | coated | 40° | RT[a] |

[a]RT = room temperature

Explants were removed at 1, 3 and 5 weeks following implantation and analyzed histologically for evidence of persistence, cellular repopulation, vascularization, and inflammation using the same criteria as described in Example 2. Histological analyses indicated that all the coated materials remained intact during the entire 5 week implantation period. All the coated materials were repopulated and revascularized. The level of inflammatory response induced by the coated mesh samples (Samples B-F) appeared to be relatively reduced compared to that induced by the uncoated mesh (Sample A). Only a mild to moderate inflammation was noted with all the coated mesh samples. This experiment confirmed that mild heat treatment of the ATM, which resulted in increased biomechanical strength of the coated mesh, did not affect the in vivo activity of the resulting coated mesh samples.

Example 8

Biochemical Analysis of Dermal Films

The effect of preparation temperature on the biochemical composition of dermal films was evaluated. In brief, dermal films were prepared, as described in Example 5, with ATM that had been swollen in 0.1 M acetic acid at either room temperature, 32° C., 37° C., or 40° C.; the films were dried at room temperature. The biochemical composition of the resulting dermal films was compared with that of micronized ATM.
Collagen Analysis.

The collagen content of dermal films was evaluated quantitatively, by hydroxyproline analysis, and qualitatively, by SDS-polyacrylamide gel electrophoresis. For hydroxyproline analysis, dermal films were sequentially treated with salt, 0.5 M acetic acid and pepsin digestion and the soluble fractions of each were analyzed for hydroxyproline content. The Hydroxyproline content of salt, acid and pepsin fractions was determined following hydrolysis in 6 N hydrochloric acid for 24 hours at 110° C. Hydrolyzed samples were diluted with distilled water to a final concentration of 0.1 N HCl. Assay buffer (45.6 g/l sodium acetate trihydrate, 30 g/l tri-sodium citrate dihydrate, 4.4 g/l citric acid, 308.4 ml/l isopropanol and 1.4% chloramine T) was then added along with additional isopropanol and Ehrlich's reagent (2 g para-dimethylamine-benzaldehyde in 60% (v/v) perchloric acid, isopropanol; 3:13). Samples were heated at 60° C. for 25 minutes, allowed to cool and the absorbance at 540 nm was determined. Hydroxyproline was quantified by comparing the absorbance of the test samples with that of a standard curve using known concentrations of hydroxyproline. The hydroxyproline content of the extracted fractions is shown in Table 8. Hydroxyproline is expressed as a percentage of total recovered hydroxyproline.

TABLE 8

Hydroxyproline distribution (%) in Dermal Films

| | Sample | | | | |
| --- | --- | --- | --- | --- | --- |
| Fraction | Micronized ATM | Acid swollen ATM (RT) | Acid swollen ATM (32° C.) | Acid swollen ATM (37° C.) | Acid swollen ATM (40° C.) |
| Salt-extracted | 9 | 25 | 33 | 31 | 27 |
| Acid-extracted | 14 | 4 | 4 | 2 | 2 |
| Pepsin-digested | 77 | 71 | 63 | 67 | 71 |

The data shown in Table 8 indicate that, based upon the relative hydroxyproline distribution, all the dermal film samples showed an increase in the levels of salt extractable collagen and a decrease in the levels of acid extractable collagen relative to those found in the micronized ATM. No significant shift was observed for pepsin-soluble collagen. These data indicated that the collagen distribution in the major pepsin soluble fraction was not significantly altered during the process used to create the films. The acid treatment used to create the films seemed to shift the distribution of the collagen from the acid extractable to the salt extractable fraction.

The pepsin-solubilized collagen obtained from dermal film samples was analyzed by SDS-polyacrylamide gel electrophoresis (SDS-PAGE). SDS-PAGE was performed according to standard methods. Samples of purified collagen type I, purified collagen type III, pepsin-solubilized collagen from the micronized ATM starting material, and pepsin-solubilized collagen from dermal films prepared with ATM that had been swollen in 0.1 M acetic acid at either room temperature, 32° C., 37° C., or 40° C. were compared. No qualitative differences, such as, for example, differences due to collagen cross-linking or degradation, in collagen profiles were noted between the micronized ATM and any of the dermal film samples. The micronized ATM and the dermal film samples were composed primarily of type I and type III collagens.
Proteoglycan (Decorin) Analysis.

Proteoglycans were extracted from micronized ATM starting material and from dermal films prepared with ATM that had been swollen in 0.1 M acetic acid at either room temperature, 32° C., or 37° C. Proteoglycans were resolved by SDS-PAGE and transferred to a membrane for immunoblotting. Immunoblotting was performed according to standard methods. The membrane was probed with a decorin-specific polyclonal antibody. Comparable levels of decorin were detectable in all the samples; no evidence of degradation or cross-linking was noted.

Glycosaminoglycan Analysis.

Glycosaminoglycans were extracted from micronized ATM starting material and from dermal films prepared with ATM that had been swollen in 0.1 M acetic acid at either room temperature, 32° C., 37° C., or 40° C. Glycosaminoglycans were resolved by cellulose acetate electrophoresis according to standard methods. Hyaluronic acid and chondroitin sulfate glycosaminoglycans were detectable in all samples and no qualitative differences in glycosaminoglycan profiles were observed.

Example 9

Biomechanical Analysis of Dermal Films

The effect of preparation temperature on the biomechanical properties of dermal films was evaluated. In brief, dermal films were prepared with ATM that had been swollen in 0.1 M acetic acid at either room temperature, 32° C., 37° C., or 40° C., as described in Example 5, dried in a nitrogen atmosphere, and 1 cm strips of the dermal films were subjected to tensile testing using an Instron 5865 testing machine (Instron Corporation, Norwood, Mass.). The data shown in Table 9 indicate that films prepared with ATM that had been swollen at elevated temperatures had increased tensile strength relative to films that had been prepared with ATM that had been swollen at room temperature. The optimum temperature for maximum gain in biomechanical properties was approximately 37° C. Thus, for example, the maximum stress for films prepared with mesh that had been swollen at room temperature was 0.017±0.007 MPa; the corresponding value for films prepared with mesh that had been swollen at 37° C. was 0.123±0.009 MPa. The Young's modulus for films prepared with mesh that had been swollen at room temperature was 9.25±0.096 MPa; the corresponding value for films prepared with mesh that had been swollen at 37° C. was 46.0±3.00 MPa. The maximal load for films prepared with mesh that had been swollen at room temperature was 0.056±0.002 N; the corresponding value for films prepared with mesh that had been swollen at 37° C. was 0.0.337±0.024 N. The percent strain for films prepared with mesh that had been swollen at room temperature was 21.1±1.0%; the corresponding value for films prepared with mesh that had been swollen at 37° C. was 49.3±3.5%.

Example 10

In Vivo Analysis of Coated Mesh in a Rat Hernia Model System

The biocompatibility of the coated mesh was also evaluated in a clinically relevant rat hernia model system. Full thickness excisional defects (about 1.5 cm×2.5 cm) were created in the fascia of the ventral abdominal wall of rats. The defects was repaired by placing a 3 cm×5 cm oval shaped test article (polypropylene or hybrid) mesh into an underlay position and fixing the mesh at the wound edge by sutures. Film coated mesh was prepared essentially according to the method described in Example 5. The ATM was swollen at 37° C. and poured into polystyrene dishes. The mesh was immersed in the ATM solution to a depth of 0.5 cm; 0.75 mg ATM/cm$^2$ of polypropylene mesh was used. For these experiments, a large piece of mesh (about 11 cm×18 cm) was coated as described above, dried at ambient temperature and then and cut into small (3 cm×5 cm) ovals prior to implantation). Samples were not cross-linked.

Excisional defects (about 1.5 cm×2.5 cm) were created in the abdomens of rats and repaired with either polypropylene mesh or hybrid hernia mesh using a tension free underlay technique. Defects were created by removing an oval shape piece of fascial tissue using scissors. Mesh test articles were inserted into the defect and tacked at the wound edge using 6 evenly spaced sutures. The study used 16 rats, with 8 rats receiving polypropylene implants and 8 rats receiving hybrid mesh implants. Five rats in each group were analyzed 4 weeks after implantation and the remaining 3 rats at 8 weeks after implantation. For analysis, explants were collected and subjected to both gross and histological evaluation. Percent coverage of surface area was estimated by an investigator who was blind as to the identity of each sample. Extensive omental adhesions were observed upon inspection of the polypropylene explants (approximately 65% surface area involvement); omental adhesions generated by the coated mesh explants involved only about 18% of the surface area. In addition, visceral (liver and gut) adhesions were noted in two of the animals repaired with polypropylene mesh and were absent from animals repaired with the hybrid mesh. Indicators of a regenerative response, including cell repopulation, revascularization, minimal inflammation and graft persistence, were observed upon histological analysis of the hybrid mesh samples at 4 weeks post-implantation. All coated test articles (with the exception of two samples that contained active infections) were characterized by repopulation with fibroblast-like cells, revascularization, minimal inflammation and persistence of the biologic coating. In contrast, the polypropylene test articles were associated with a greater cellular

TABLE 9

Biomechanical properties of Dermal Films

| Parameter | Sample | | | |
|---|---|---|---|---|
| | Acid swollen ATM (RT) | Acid swollen ATM (32° C.) | Acid swollen ATM (37° C.) | Acid swollen ATM (40° C.) |
| Maximum stress (MPa) | 0.017 ± 0.007 | 0.094 ± 0.025 | 0.123 ± 0.009 | 0.082 ± 0.024 |
| Young's modulus (MPa) | 9.25 ± .096 | 39.00 ± 9.00 | 46.0 ± 3.00 | 29.75 ± 8.88 |
| Maximum Load (N) | 0.056 ± 0.002 | 0.291 ± 0.087 | 0.337 ± 0.024 | 0.214 ± 0.062 |
| Percent strain | 21.1 ± 1.0 | 46.6 ± 3.0 | 49.3 ± 3.5 | 48.5 ± 3.4 | response around the polypropylene fibers consistent with an aggressive foreign body response to the implanted mesh test articles.

Example 11

Preparation of Film-Coated Mesh Using ATM Procured from Yorkshire Pigs

ATM was prepared according to the method described in Example 1, except that the dermal tissue was procured from Yorkshire pigs. The ATM was micronized and then washed in water to remove soluble cryoprotectant. The micronized ATM was swollen for 3 hours at 37° C. according to the method in Example 1, except that the swelling took place in 40 mM HCl (pH 1.4) instead of 100 mM acetic acid. Polypropylene mesh was coated as described in Example 2 and dried at room temperature The biocompatibility of the coated mesh was evaluated in a rat hernia model system as described in Example 8. Indicators of a regenerative response, including cell repopulation, revascularization, minimal inflammation, were observed upon histological analysis of the hybrid mesh samples at 4 weeks post-implantation.

What is claimed is:

1. A method of making a biocompatible mesh composition, the method comprising:
   a) selecting a tissue;
   b) preparing an acellular tissue matrix (ATM) by treating the tissue to remove cellular material from the tissue, wherein the ATM retains biological functions which are provided by undenatured collagenous proteins and non-collagenous molecules;
   c) processing the ATM to produce a plurality of particles, of intact ATM;
   d) incubating the plurality of particles of intact ATM in an acidic solution to create a suspension of swollen ATM particles of intact ATM, wherein the acidic solution has a pH from about 1.0 to about 3.0; and
   e) applying the suspension to a biocompatible mesh substrate composition and drying the composition to create a coated mesh substrate.

2. The method of claim 1, wherein steps (d) and (e) are performed simultaneously.

3. The method of claim 1, wherein the tissue is dermis.

4. The method of claim 1, wherein the tissue is selected from the group consisting of fascia, pericardial tissue, dura, umbilical cord tissue, placental tissue, cardiac valve tissue, ligament tissue, tendon tissue, arterial tissue, venous tissue, neural connective tissue, urinary bladder tissue, ureter tissue, and intestinal tissue.

5. The method of claim 1, wherein the tissue is human tissue.

6. The method of claim 1, wherein the tissue is made from non-human mammalian tissue.

7. The method of claim 6, wherein the non-human mammalian tissue is obtained from a pig.

8. The method of claim 6, wherein the tissue is obtained from a non-human mammal that is genetically engineered to lack expression of α-1,3-galactosyl epitopes.

9. The method of claim 8, wherein the non-human mammal lacks a functional α-1,3-galactosyltransferase gene.

10. The method of claim 1, wherein the pH is from about 1.5 to about 2.5.

11. The method of claim 1, wherein the pH is about 1.4.

12. The method of claim 1, wherein the acidic solution is a solution comprising an acid selected from the group consisting of acetic acid, ascorbic acid, boric acid, carbonic acid, citric acid, hydrochloric acid, lactic acid, tannic acid, phosphoric acid, and sulfuric acid.

13. The method of claim 1, wherein the acidic solution comprises 0.1 M acetic acid.

14. The method of claim 1, wherein the acidic solution comprises 0.04 M hydrochloric acid.

15. The method of claim 1, wherein the incubation step is for a period from about 0.5 hours to about 12 hours.

16. The method of claim 1, wherein the incubation step is for a period from about 1.0 to about 10.0 hours.

17. The method of claim 1, wherein the incubation step is for a period from about 2.0 to about 6.0 hours.

18. The method of claim 1, wherein the incubation step is for a period from about 2.5 to about 5.0 hours.

19. The method of claim 1, wherein the incubation step is for a period of about 3.0 hours.

20. The method of claim 1, wherein the incubating step, the drying step, or the incubating and the drying steps are at a temperature of about 20° C. to about 42° C.

21. The method of claim 1, wherein the incubating step, the drying step, or the incubating and the drying steps are at a temperature of about 20° C. to about 30° C.

22. The method of claim 1, wherein the incubating step, the drying step, or the incubating and the drying steps are at a temperature of about 25° C. to about 35° C.

23. The method of claim 1, wherein the incubating step, the drying step, or the incubating and the drying steps are at a temperature of about 30° C. to about 40° C.

24. The method of claim 1, wherein the incubating step, the drying step, or the incubating and the drying steps are at a temperature of about 35° C. to about 38° C.

25. The method of claim 1, wherein the incubating step, the drying step, or the incubating and the drying steps are at a temperature of about 37° C. to about 42° C.

26. The method of claim 1, wherein the incubating step, the drying step, or the incubating and the drying steps are at a temperature of about 37° C.

27. The method of claim 1, wherein the incubating step, the drying step, or the incubating and the drying steps are at a temperature of about 25° C.

28. The method of claim 1, wherein the biocompatible mesh substrate is non-absorbable.

29. The method of claim 1, wherein the biocompatible mesh substrate is absorbable.

30. The method of claim 29, wherein the biocompatible mesh substrate is a polymer.

31. The method of claim 30, wherein the polymer comprises poly-4-hydroxybutyrate.

32. The method of claim 29, wherein the absorbable biocompatible mesh substrate is a polymer selected from the group consisting of polyhydroxyalkanoate, polyglycolic acid, poly-l-lactic acid, polylactic/polyglycolic acid (PLGA), polygalactin 910, and carboxymethyl cellulose.

33. The method of claim 1, wherein the biocompatible mesh substrate is a synthetic substrate.

34. The method of claim 33, wherein the synthetic substrate comprises polypropylene.

35. The method of claim 1, wherein the drying step comprises drying in a nitrogen atmosphere.

36. The method of claim 1, wherein the drying step comprises freeze-drying.

37. The method of claim 1, wherein treating the tissue to remove cellular material from the tissue includes removal of all cellular material.

38. The method of claim 1, wherein the pH is from about 2.0 to about 3.0.

39. A biocompatible mesh composition made by the method of claim 1.

* * * * *